(12) United States Patent
Shiraki et al.

(10) Patent No.: US 10,344,014 B2
(45) Date of Patent: Jul. 9, 2019

(54) AMORPHOUS FORM OF TETRACYCLIC COMPOUND

(71) Applicant: Chugai Seiyaku Kabushiki Kaisha, Kita-Ku, Tokyo (JP)

(72) Inventors: Koji Shiraki, Shizuoka (JP); Tadanobu Nakayama, Tokyo (JP); Tomoaki Ota, Tokyo (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/501,267

(22) PCT Filed: Aug. 7, 2015

(86) PCT No.: PCT/JP2015/072450
§ 371 (c)(1),
(2) Date: Feb. 2, 2017

(87) PCT Pub. No.: WO2016/021707
PCT Pub. Date: Feb. 11, 2016

(65) Prior Publication Data
US 2017/0217927 A1    Aug. 3, 2017

(30) Foreign Application Priority Data

Aug. 8, 2014 (JP) .................. 2014-162899

(51) Int. Cl.
| A61K 9/10 | (2006.01) |
|---|---|
| A61K 47/32 | (2006.01) |
| A61K 47/38 | (2006.01) |
| C07D 401/04 | (2006.01) |
| C07D 401/10 | (2006.01) |
| A61K 31/5377 | (2006.01) |

(52) U.S. Cl.
CPC ............. *C07D 401/10* (2013.01); *A61K 9/10* (2013.01); *A61K 47/32* (2013.01); *A61K 47/38* (2013.01); *C07D 401/04* (2013.01); *A61K 31/5377* (2013.01)

(58) Field of Classification Search
CPC .......... A61K 9/10; A61K 47/32; A61K 47/38; A61K 401/04; A61K 401/10; A61K 31/5377
See application file for complete search history.

(56) References Cited

U.S. PATENT DOCUMENTS

| 5,721,267 A | 2/1998 | Broka |
|---|---|---|
| 5,936,084 A | 8/1999 | Jirousek et al. |
| 9,126,931 B2 | 9/2015 | Kinoshita et al. |
| 9,365,514 B2 | 6/2016 | Furumoto et al. |
| 9,440,922 B2 | 9/2016 | Kinoshita et al. |
| 2004/0076675 A1 | 4/2004 | Sugishita et al. |
| 2005/0107364 A1 | 5/2005 | Hutchinson et al. |
| 2007/0031907 A1 | 2/2007 | Pinna et al. |
| 2007/0065516 A1 | 3/2007 | Sugishita et al. |
| 2007/0099893 A1 | 5/2007 | Boyd et al. |
| 2007/0249653 A1 | 10/2007 | Jagtap et al. |
| 2008/0058320 A1 | 3/2008 | Herold et al. |
| 2008/0090776 A1 | 4/2008 | Mano et al. |
| 2008/0262021 A1 | 10/2008 | Capraro et al. |
| 2009/0099193 A1 | 4/2009 | Mano et al. |
| 2009/0221555 A1 | 9/2009 | Ahmed et al. |
| 2010/0099658 A1 | 4/2010 | Kondoh et al. |
| 2010/0240673 A1 | 9/2010 | Mano et al. |
| 2011/0230545 A1 | 9/2011 | Mano et al. |
| 2012/0083488 A1 | 4/2012 | Kinoshita et al. |
| 2013/0143877 A1 | 6/2013 | Furumoto et al. |
| 2013/0158095 A1 | 6/2013 | Mano et al. |
| 2015/0184161 A1 | 7/2015 | Mano et al. |
| 2015/0272958 A1 | 10/2015 | Kodama et al. |
| 2016/0317494 A1 | 11/2016 | Furumoto et al. |
| 2016/0340308 A1 | 11/2016 | Kinoshita et al. |
| 2017/0035773 A1 | 2/2017 | Tomimatsu et al. |
| 2017/0081306 A1 | 3/2017 | Tanaka et al. |
| 2017/0119781 A1 | 5/2017 | Meier et al. |

FOREIGN PATENT DOCUMENTS

| CA | 2885733 A | 9/2015 |
|---|---|---|
| CN | 1902200 A | 1/2007 |
| EA | 001450 B1 | 4/2001 |
| EP | 1914240 B1 | 4/2008 |
| EP | 2441753 * | 4/2012 |
| EP | 2606886 * | 6/2013 |
| EP | 3135671 A1 | 3/2017 |
| JP | 08-092090 A | 4/1996 |
| JP | 2008-280352 A | 11/2008 |
| JP | 2009-100783 A | 5/2009 |
| JP | 4588121 B1 | 9/2010 |
| JP | 4918630 B1 | 2/2012 |
| JP | 2012-126711 A | 7/2012 |
| RU | 2162089 C2 | 1/2001 |

(Continued)

OTHER PUBLICATIONS

Scifinder printout of structures of EP 2441753.*
Bunz, F., "Chapter 1, The Genetic Basis of Cancer," Principles of Cancer Genetics, 2008, 1-47.
CAS RN 100863-39-6, STN Entry Date Mar. 15, 1986.
CAS RN 222318-66-3, STN Entry Date May 7, 1999.
CAS RN 24716-14-1, STN Entry Date Nov. 16, 1984.
CAS RN 36263-63-5, STN Entry Date Nov. 16, 1984.
CAS RN 4355-38-8, STN Entry Date Nov. 16, 1984.
CAS RN 6008-29-3, STN Entry Date Nov. 16, 1984.
CAS RN 61492-49-7, STN Entry Date Nov. 16, 1984.
CAS RN 74205-47-3, STN Entry Date Nov. 16, 1984.
CAS RN 89579-57-7, STN Entry Date Nov. 16, 1984.
CAS RN 93257-39-7, STN Entry Date Dec. 18, 1984.
Chen et al., "Oncogenic mutations of ALK kinase in neuroblastoma," Nature, Oct. 16, 2008, 455:971-974, and Methods page.

(Continued)

*Primary Examiner* — Shirley V Gembeh
(74) *Attorney, Agent, or Firm* — Foley & Lardner LLP

(57) ABSTRACT

An amorphous form of 9-ethyl-6,6-dimethyl-8-(4-morpholin-4-yl-piperidin-1-yl)-11-oxo-6,11-dihydro-5H-benzo[b]carbazole-3-carbonitrile and a solid dispersion containing the amorphous form can be used extremely advantageously as drugs for oral administration.

13 Claims, 9 Drawing Sheets

(56) References Cited

FOREIGN PATENT DOCUMENTS

| | | |
|---|---|---|
| WO | WO 00/69856 A1 | 11/2000 |
| WO | WO 2004/080980 A1 | 9/2004 |
| WO | WO 2005/009389 A2 | 2/2005 |
| WO | WO 2005/097765 A1 | 10/2005 |
| WO | WO 2006/021884 A2 | 3/2006 |
| WO | WO 2007/023310 A2 | 3/2007 |
| WO | WO 2007/056497 A1 | 5/2007 |
| WO | WO 2007/130468 A2 | 11/2007 |
| WO | WO 2008/021369 A2 | 2/2008 |
| WO | WO 2008/051547 A1 | 5/2008 |
| WO | WO 2008/130951 A1 | 10/2008 |
| WO | WO 2009/008371 A1 | 1/2009 |
| WO | WO 2009/013126 A1 | 1/2009 |
| WO | WO 2009/073620 A2 | 6/2009 |
| WO | WO 2010/128324 A1 | 11/2010 |
| WO | WO 2010/142423 A2 | 12/2010 |
| WO | WO 2010/142685 A1 | 12/2010 |
| WO | WO 2014/050781 A1 | 4/2014 |
| WO | WO 2015/163447 A1 | 10/2015 |

OTHER PUBLICATIONS

Cools et al., "Identification of Novel Fusion Partners of ALK, the Anaplastic Lymphoma Kinase, in Anaplastic Large-Cell Lymphoma and Inflammatory Myofibroblastic Tumor," Genes, Chromosomes & Cancer, 2002, 34:354-362.
Druker et al., "Section 1: Chronic Myelogenous Leukemia," Cancer: Principles & Practice of Oncology, 7$^{th}$ Edition (DeVita et al., Eds.), 2121.
Faderl et al., "Section 3: Myelodysplastic Syndromes," Cancer: Principles & Practice of Oncology, 7$^{th}$ Edition (DeVila et al., Eds.), 2144.
Fine et al., "Section 2: Neoplasms of the Central Nervous System," Cancer: Principles & Practice of Oncology, 7$^{th}$ Edition (DeVita et al., Eds.), 1834-1887.
Fischer et al., "A Ki-1(CD30)-Positive Human Cell Line (Karpas 299) Established From a High-Grade Non-Hodgkin's Lymphoma, Showing a 2;5 Translocation and Rearrangement of the T-Cell Receptor β-Chain Gene," Blood, Jul. 1988, 72(1):234-240.
Galkin et al., "Identification of NVP-TAE684, a potent, selective and efficacious inhibitor of NPM-ALK," PNAS, Jan. 2, 2007, 104(1):270-275 (and Corrections published in PNAS, Feb. 6, 2007, 104(6):2024-2025).
Garbett et al., "Extending Nature's Leads: The Anticancer Agent Ellipticine," Curr. Med. Chem.—Anti-Cancer Agents, 2004, 4:149-172.
George et al., "Activating mutations in ALK provide a therapeutic target in neuroblastoma," Nature, 2008, 455:975-978.
Girouard et al., "Neurovascular coupling in the normal brain and in hypertension, stroke, and Alzheimer disease," Journal of Applied Physiology, 2006, 100:328-335.
Glick et al., "Treatment with atypical antipsychotics: new indications and new populations," Journal of Psychiatric Research, 2001, 35:187-191.
Goel et al., "Mice transgenic for BRAF V600E demonstrate phenotype affecting melanocyte and neural lineages," Proceedings of the American Association for Cancer Research, Apr. 2006, 47:#273.
Goodman & Gilman's, Chemotherapy of Neoplastic Diseases, The Pharmacological Basis of Therapeutics, Brunton et al., Eds., 2008, 11$^{th}$ Ed., 853-908.
Griffin et al., "Recurrent Involvement of 2p23 in Inflammatory Myofibroblastic Tumors," Cancer Research, Jun. 15, 1999, 59:2776-2780.
Herbst et al., "ALK Gene Products in Anaplastic Large Cell Lymphomas and Hodgkin's Disease," Blood, Sep. 1, 1995, 86(5):1694-1700.
Huang et al., "An in vivo model to study human GSTP1 polymorphisms in osteosarcoma," Proceedings of the American Association for Cancer Research, Apr. 2006, 47:#271.

Hübinger et al., "CD30-mediated cell cycle arrest associated with induced expression of p21$^{CIP1/WAF1}$ in the anaplastic large cell lymphoma cell line Karpas 299," Oncogene, 2001, 20:590-598.
Jazii et al., "Identification of squamous cell carcinoma associated proteins by proteomics and loss of beta tropomyosin expression in esophageal cancer," World J. Gastroenterol., Nov. 28, 2006, 12(44):7104-7112.
Kirsch, Gilbert H., "Heterocyclic Analogues of Carbazole Alkaloids," Current Organic Chemistry, 2001, 5:507-518.
Kuppen et al., "Tumor structure and extracellular matrix as a possible barrier for therapeutic approaches using immune cells or adenoviruses in colorectal cancer," Histochem. Cell. Biol., 2001, 115:67-72.
Kuster, Bernhard, Ed., Kinase Inhibitors, Methods and Protocols, Methods in Molecular Biology, 2012, vol. 795, Chapter 1 by Fabbro et al., "Targeting Cancer with Small-Molecular-Weight Kinase Inhibitors."
Kwak et al., "Anaplastic Lymphoma Kinase Inhibition in Non-Small-Cell Lung Cancer," The New England Journal of Medicine, Oct. 28, 2010, 363(18):1693-1703.
Lamant et al., "Establishment of a novel anaplastic large-cell lymphoma-cell line (COST) from a 'small-cell variant' of ALCL," Leukemia, 2004, 18:1693-1698.
Lissoni et al., "Biotherapy with the pineal hormone melatonin plus aloe and myrrh tincture in untreatable metastatic cancer patients as an essence therapy of cancer," Cancer Therapy, 2009, 7:397-401.
Luo et al., "Principles of Cancer Therapy: Oncogene and Non-oncogene Addiction," Cell, Mar. 6, 2009, 136:823-837.
Mosse et al., "Identification of ALK as a major familial neuroblastoma predisposition gene," Nature, Oct. 16, 2008, 455:930-935, and Methods page.
National Cancer Institute, http://www.cancer.gov/, "A to Z List of Cancers," downloaded May 29, 2014, 22 pages.
O'Brien et al., "Section 2: Chronic Lymphoid Leukemias," Cancer: Principles & Practice of Oncology, 7$^{th}$ Edition (DeVita et al., Eds.), 2133.
O'Brien et al., "Vascular cognitive impairment," The Lancet Neurology, Feb. 2003, 2:89-98.
Pao et al., "EGF receptor gene mutations are common in lung cancers from 'never smokers' and are associated with sensitivity of tumors to gefitinib and erlotinib," PNAS, Sep. 7, 2004, 101(36):13306-13311.
Piva et al., "Ablation of oncogenic ALK is a viable therapeutic approach for anaplastic large-cell lymphomas," Blood, Jan. 2006, 107(2):689-697.
Rosenwald et al., "t(1;2)(q21;p23) and t(2;3)(p23;q21): Two Novel Variant Translocations of the t(2;5)(p23;q35) in Anaplastic Large Cell Lymphoma," Blood, Jul. 1, 1999, 94(1):362-364.
Scheinberg et al., "Section 2: Management of Acute Leukemias," Cancer: Principles & Practice of Oncology, 7$^{th}$ Edition (DeVita et al., Eds.), 2005, 2088, 2092.
Shah et al., "Current approaches in the treatment of Alzheimer's disease," Biomedicine & Pharmacotherapy, 2008, 62:199-207.
Shaw et al., "Targeting Anaplastic Lymphoma Kinase in Lung Cancer," Clinical Cancer Research, 2011, 17:2081-2086.
Shujuan, Wang, "The new insights on the diagnosis of malignant histiocytosis," Chinese Journal of Laboratory Medicine, Jan. 30, 2005, 28(1):14-16.
Silverman, Richard B., The Organic Chemistry of Drug Design and Drug Action, Second Ed., Elsevier Academic Press, Northwestern University, Evanston, Illinois, 2004, 29-31, table 2.2.
Soussi, Thierry, "p53 Antibodies in the Sera of Patients with Various Types of Cancer: A Review," Cancer Res., 2000, 60:1777-1788.
Stoica et al., "Identification of Anaplastic Lymphoma Kinase as a Receptor for the Growth Factor Pleiotrophin," J. Biol. Chem., May 18, 2001, 276(20:16772-16779.
Stoica et al., "Midkine Binds to Anaplastic Lymphoma Kinase (ALK) and Acts as a Growth Factor for Different Cell Types," J. Biol. Chem., Sep. 27, 2002, 277(39):35990-35998.
Wanner et al., "A convenient synthesis of 6-methylellipticine and 6-methylolivacine," Heterocycles, 1982, 19(12):2295-2300.
Wood et al., "Lack of the t(2;5) or Other Mutations Resulting in Expression of Anaplastic Lymphoma Kinase Catalytic Domain in

(56) References Cited

OTHER PUBLICATIONS

CD30+Primary Cutaneous Lymphoproliferative Disorders and Hodgkin's Disease," Blood, Sep. 1, 1996, 88(5):1765-1770.

Zhao et al., "The progress of the research on anaplastic lymphoma kinase genetic abnormality of anaplastic large cell lymphoma," Foreign Medical Sciences (Section of Blood Transfusion and Hematology), Oct. 15, 2004, 27(5):403-406.

Ahlneck et al., "The molecular basis of moisture effects on the physical and chemical stability of drugs in the solid state," International Journal of Pharmaceutics, 1990, 62:87-95.

Bilsland et al., "Behavioral and Neurochemical Alterations in Mice Deficient in Anaplastic Lymphoma Kinase Suggest Therapeutic Potential for Psychiatric Indications," Neuropsychopharmacology, 2008, 33:685-700.

Byrn et al., "Pharmaceutical Solids: A Strategic Approach to Regulatory Considerations," Pharmaceutical Research, 1995, 12(7):945-954.

Caira, Mino R., "Crystalline Polymorphism of Organic Compounds," Topics in Current Chemistry, 1998, 198:163-208.

Haleblian, John K., "Characterization of Habits and Crystalline Modification of Solids and Their Pharmaceutical Applications," Journal of Pharmaceutical Sciences, 1985, 64(8):1269-1288.

Hancock et al., "Characteristics and Significance of the Amorphous State in Pharmaceutical Systems," Journal of Pharmaceutical Sciences, 1997, 86(1):1-12.

Kinoshita et al., "Design and synthesis of a highly selective, orally active and potent anaplastic lymphoma kinase inhibitor (CH5424802)," Bioorganic & Medicinal Chemistry, 2012, 20(3):1271-1280.

Soda et al., "Identification of the transforming EML4-ALK fusion gene in non-small-cell lung cancer," Nature, 2007, 448:561-566.

Caron et al., "A Comparison of Spray Drying and Milling in the Production of Amorphous Dispersions of Sulfathiazole/Polyvinylpyrrolidone and Sulfadimidine/Polyvinylpyrrolidone," Molecular Pharmaceutics, Feb. 16, 2011, 8(2):532-542.

Elkhabaz, Ahmed, "Understanding, characterization, and development of amorphous solid dispersions for poorly water-soluble drugs," Drug Innovation Master Program, Jun. 23, 2014-Jul. 25, 2014, Department of Pharmaceuticals, Utrecht Institute for Pharmaceutical Sciences, Utrecht University, The Netherlands, 40 pages.

* cited by examiner

DSC

AMORPHOUS FORM OF TETRACYCLIC COMPOUND

CROSS-REFERENCE TO RELATED APPLICATIONS

This application is a National Stage application of PCT/JP2015/072450, filed Aug. 7, 2015, which claims priority from Japanese application JP 2014-162899, filed Aug. 8, 2014.

TECHNICAL FIELD

The present invention relates to amorphous forms of tetracyclic compounds having inhibitory activity on ALK, and solid dispersions containing the amorphous forms.

BACKGROUND ART

Anaplastic lymphoma kinase (ALK) is one of receptor tyrosine kinases belonging to the insulin-receptor family (NPL 1 and NPL 2), and an abnormality in the ALK gene has been reported to lead to the production of an abnormal kinase with the gene fused with another gene.

As diseases with abnormalities of ALK, cancer and cancer metastasis (NPL 1 and PTL 1), depression, and cognitive function disorders (NPL 2) are known. Accordingly, provision of ALK inhibitors will results in that of effective therapeutic and prophylactic agents against these diseases.

As compounds having inhibitory activity on ALK, a compound represented by the formula (I) (compound name: 9-ethyl-6,6-dimethyl-8-(4-morpholin-4-yl-piperidin-1-yl)-11-oxo-6,11-dihydro-5H-benzo[b]carbazole-3-carbonitrile) and the like are known (PTL 2, PTL 3, and PTL 4).

Since the compound is poorly soluble or insoluble to water, a sufficient bioavailability might not possibly be obtained when it is administered orally.

CITATION LIST

Patent Literature

PTL 1: Japanese Patent Laid-Open No. 2009100783(A)
PTL 2: Japanese Patent No. 4588121
PTL 3: Japanese Patent No. 4918630
PTL 4: Japanese Patent Laid-open No. 2012-126711

Non Patent Literature

NPL 1: Nature, vol. 448, pp. 561-566, 2007
NPL 2: Neuropsychopharmacology, vol. 33, pp. 685-700, 2008

SUMMARY OF INVENTION

Technical Problem

With respect to the aforementioned problem, the present inventors found, as a result of extensive studies, that amorphous forms of hydrochlorides of the tetracyclic compound represented by the formula (I) below have a very high physical stability and an excellent solubility. Furthermore, the present inventors found that solid dispersions containing the amorphous forms have excellent physical and chemical stabilities and solubility of the compound represented by the formula (I), a salt thereof, or a solvate of the compound or a salt thereof is improved.

Solution to Problem

More specifically, the present invention is as follows.
(1) An amorphous form of a compound represented by the formula (I):

[Chemical formula 1]

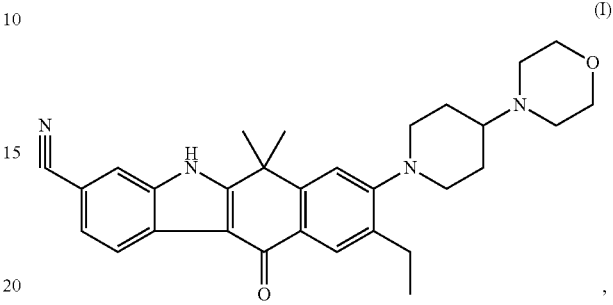

a salt thereof, or a solvate of the compound or a salt thereof.
(2) The amorphous form described in (1), wherein the amorphous form includes a salt of the compound.
(3) The amorphous form described in (1) or (2), wherein the salt is a hydrochloride.
(4) The amorphous form described in any one of (1) to (3), wherein the salt is a monohydrochloride.
(5) The amorphous form described in any one of (1) to (4), wherein an exothermic peak is detected between 190°±5° C. and 230°±5° C. by a differential scanning calorimetry analysis.
(6) The amorphous form described in any one of (1) to (4), wherein a glass transition temperature is between 190±5° C. and 230±5° C.
(7) The amorphous form described in any one of (1) to (6), wherein the amorphous form has an X-ray powder diffraction pattern shown in FIG. 1.
(8) A method of producing an amorphous form of a compound represented by the formula (I), a salt thereof, or a solvate of the compound or a salt thereof, the method including the steps of: (i) dissolving the compound represented by the formula (I), the salt thereof, or the solvate of the compound or the salt thereof into a solvent to prepare a feed solution; (ii) spraying the feed solution obtained in the step (i); and (iii) drying the sprayed feed solution to provide the amorphous form of the compound represented by the formula (I), a salt thereof, or a solvate of the compound or a salt thereof.
(9) The method described in (8), wherein the compound represented by the formula (I), the salt thereof, or the solvate of the compound or the salt thereof in the step (i) is a crystalline form.
(10) The method described in (8), wherein the compound represented by the formula (I), the salt thereof, or the solvate of the compound or the salt thereof comprises a hydrochloride of the compound represented by the formula (I).
(11) The method described in (9) or (10), wherein the compound represented by the formula (I), the salt thereof, or the solvate of the compound or the salt thereof comprises a monohydrochloride of the compound represented by the formula (I).
(12) The method described in (9) to (11), wherein the hydrochloride of the compound represented by the formula (I) in the step (i) is a crystalline form having an X-ray powder diffraction pattern with peaks at diffraction angles (2θ) of 8.4°±0.2°, 14.0°±0.2°, 16.7°±0.2°, 18.8°±0.2°, and 23.3°±0.2°.

(13) The method described in any one of (8) to (12), wherein the solvent is tetrahydrofuran.

(14) The method described in (13) wherein a concentration of the tetrahydrofuran is between 65% and 85%.

(15) An amorphous form of a compound represented by the formula (I), a salt thereof, or a solvate of the compound or a salt thereof, wherein the amorphous form is obtained by the method described in any one of (8) to (14).

(16) An amorphous form of a monohydrochloride of the compound represented by the formula (I), wherein the amorphous form is obtained by the method described in any one of (8) to (14).

(17) A composition including amorphous and crystalline forms of a compound represented by the formula (I), a salt thereof, or a solvate of the compound or a salt thereof.

(18) The composition described in (17), wherein a content of the crystalline form is 10% by weight or less.

(19) The composition described in (17) or (18), wherein a content of the crystalline form is 3% by weight or less.

(20) The composition described in any one of (17) to (19), wherein a content of the crystalline form is 1% by weight or less.

(21) The composition described in any one of (17) to (20), wherein the compound represented by the formula (I) or the salt thereof comprises a hydrochloride of the compound represented by the formula (I).

(22) The composition described in any one of (17) to (21), wherein the compound represented by the formula (I) or the salt thereof comprises a monohydrochloride of the compound represented by the formula (I).

(23) The composition described in any one of (17) to (22), wherein the amorphous form is detected as an exothermic peak between 190°±5° C. and 230°±5° C. by a differential scanning calorimetry analysis.

(24) The composition described in any one of (17) to (22), wherein the amorphous form has a glass transition temperature of about 190±5° C. to 230±5° C.

(25) The composition described in any one of (17) to (24), wherein the amorphous form has an X-ray powder diffraction pattern shown in FIG. 1.

(26) A solid dispersion including an amorphous form of a compound represented by the formula (I), a salt thereof, or a solvate of the compound or a salt thereof; and an inert carrier.

(27) The solid dispersion described in (26), wherein the inert carrier is a solid polymer.

(28) The solid dispersion described in (27), wherein the solid polymer is cellulose or a derivative thereof or a water-soluble synthetic polymer.

(29) The solid dispersion described in (28), wherein the solid polymer is hypromellose, hypromellose acetate succinate, hypromellose phthalate, carboxymethyl cellulose, carboxymethyl ethyl cellulose, sodium carboxymethyl cellulose, hydroxyethyl cellulose, hydroxyethyl methyl cellulose, hydroxypropyl cellulose, methyl cellulose, ethyl cellulose, cellulose acetate phthalate, polyethylene glycol, polyvinyl alcohol, povidone, copolyvidone, polyvinyl acetate phthalate, polyvinylacetal diethylamino acetate, cellulose acetate phthalate, a polyvinyl caprolactam-polyvinyl acetate-polyethylene glycol graft copolymer, an aminoalkyl methacrylate copolymer E, an aminoalkyl methacrylate copolymer RS, a methacrylate copolymer L, a methacrylate copolymer LD, a methacrylate copolymer S, or a carboxyvinyl polymer.

(30) The solid dispersion described in (29), wherein the solid polymer is selected from a polyvinyl caprolactam-polyvinyl acetate-polyethylene glycol graft copolymer, hypromellose phthalate, hypromellose acetate succinate, and a methacrylate copolymer L.

(31) The solid dispersion described in any one of (27) to (30), wherein a weight ratio of the compound represented by the formula (I), the salt thereof, or the solvate of the compound or the salt thereof; as a free form, and the inert carrier is 9:1 to 1:9.

(32) A powder, fine granules, granules, a table, or a capsule containing the solid dispersion described in any one of (26) to (31).

DESCRIPTION OF EMBODIMENTS

An "amorphous form" as used in the present invention means a state of solid substances exhibiting no definite crystalline structure. The presence or absence of a crystalline structure can be examined by measuring X-ray powder diffraction (XRPD) under the measurement conditions given below. The amorphous forms in the present invention have a diffraction pattern containing a broad and weak peak (halo) when their X-ray powder diffraction (XRPD) was measured under the measurement conditions given below. The diffraction pattern becomes more distinctive when compared with those of crystalline forms. Glass-like substances which have no crystalline structure and are similar to non-crystalline fluids with a very high viscosity are also included in the amorphous forms of the present invention.

Measurement Conditions:
Measuring instrument: X'Pert-Pro MPD (manufactured by PANalytical)
Target: Cu
Tube voltage: 45 kV
Tube current: 40 mA
Step size: 0.02°
Scan axis: 2θ
Sampling time per step: 43 sec.
Scanning range: 3 to 40°

The presence of the amorphous forms of the present invention can be examined using a well-known technique such as differential scanning calorimetry (DSC), solid NMR, X-ray (powder) diffraction, IR, NIR, and Raman spectroscopy, optionally by comparing them with a crystalline form of a compound represented by the formula (I), a salt thereof, or a solvate of the compound or a salt thereof when they are mixed with the crystalline form.

Specifically, for amorphous forms of monohydrochloride of the compound represented by the formula (I) for example, an exothermic peak is detected by a differential scanning calorimetry analysis between about 190° C. and about 230° C. The term "about" means±5° C., and preferably ±2° C. In other words, the amorphous forms of the present invention have a glass transition temperature of about 190-230° C. The term "about" means±5° C. Preferably, the glass transition temperature is about 220-230° C.

Figure 1:
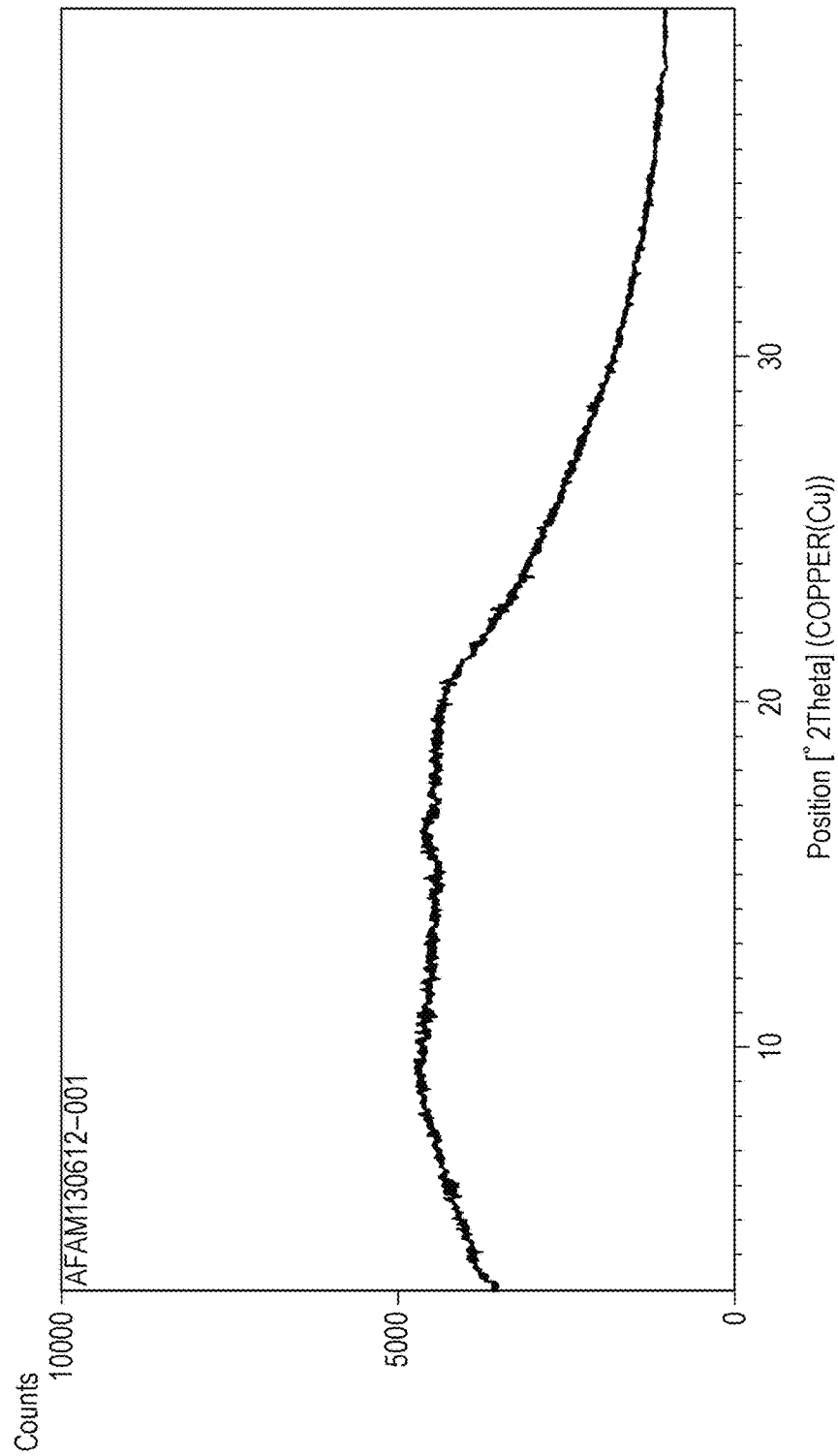
FIG. 1 is a graph showing a result of X-ray powder diffraction measurement on an amorphous form of the present invention.

When the X-ray powder diffraction is used, crystalline and amorphous forms can be discriminated easily from each other because the former exhibits a diffraction pattern containing a sharp peak whereas the latter exhibits a diffraction pattern containing a relatively broad and weak peak ("halo"). FIG. 1 shows an example of a result of X-ray powder diffraction measurement on an amorphous form of a monohydrochloride of the compound represented by the formula (I).

When differential scanning calorimetry is performed, a differential scanning calorimeter, a nitrogen gas as a purge gas, a rate of temperature rise of 10° C./min, other devices and various DSC thermograms including conditions can be used. Crystalline and amorphous forms can be discriminated from each other because the crystalline forms are typically characterized by a sharp melt endothermic/endothermic peak and amorphous forms do not exhibit a specific endothermic peak that can be found in the crystalline forms. Those skilled in the art can thus determine the presence of an amorphous form by comparing DSC thermograms between the crystalline form and the amorphous form.

Some of the measurement conditions of the differential scanning calorimetry are given below.
Instrument name: differential scanning calorimeter (DSC)
Model: Q200 (manufactured by TA Instruments)
Heating rate: 10° C./min. or 20° C./min.
Measurement temperature range: 25° C. to 350° C. (Provided that if the sample contains much residual solvent, a pre-treatment with heat at 25° C. to 125° C. or 25° C. to 175° C. may be required.)
Atmospheric gas: dry nitrogen
Flow rate of atmospheric gas: 50 mL/min.
Cell: aluminum pan (pinhole)
Sample amount: 5 mg to 10 mg
Reference standard: empty pan The amorphous form of the present invention may be in a composition, in which the amorphous form is mixed with one or more crystalline forms. The amorphous form may be in a composition in which the amorphous form is mixed with the crystalline form at any mixing rate such as about 1%, 2%, 3%, 5%, 10%, 15%, 20%, 25%, 30%, 35%, 40%, 45%, 50%, 55%, 60%, 65%, 70%, 75%, 80%, 85%, 90%, 95%, 97%, 98%, or 99% by weight or less relative to the entire composition.

The content of the crystalline form contained in the composition can be calculated using, for example, an X-ray powder diffraction method.

On the other hand, the content of the amorphous form contained in the composition can be calculated using, for example, DSC.

Examples of crystalline forms of the compound represented by the formula (I) or salts thereof include crystalline forms (form I, II, and III crystals) of monohydrochloride of the compound represented by the formula (I).

Figure 2:
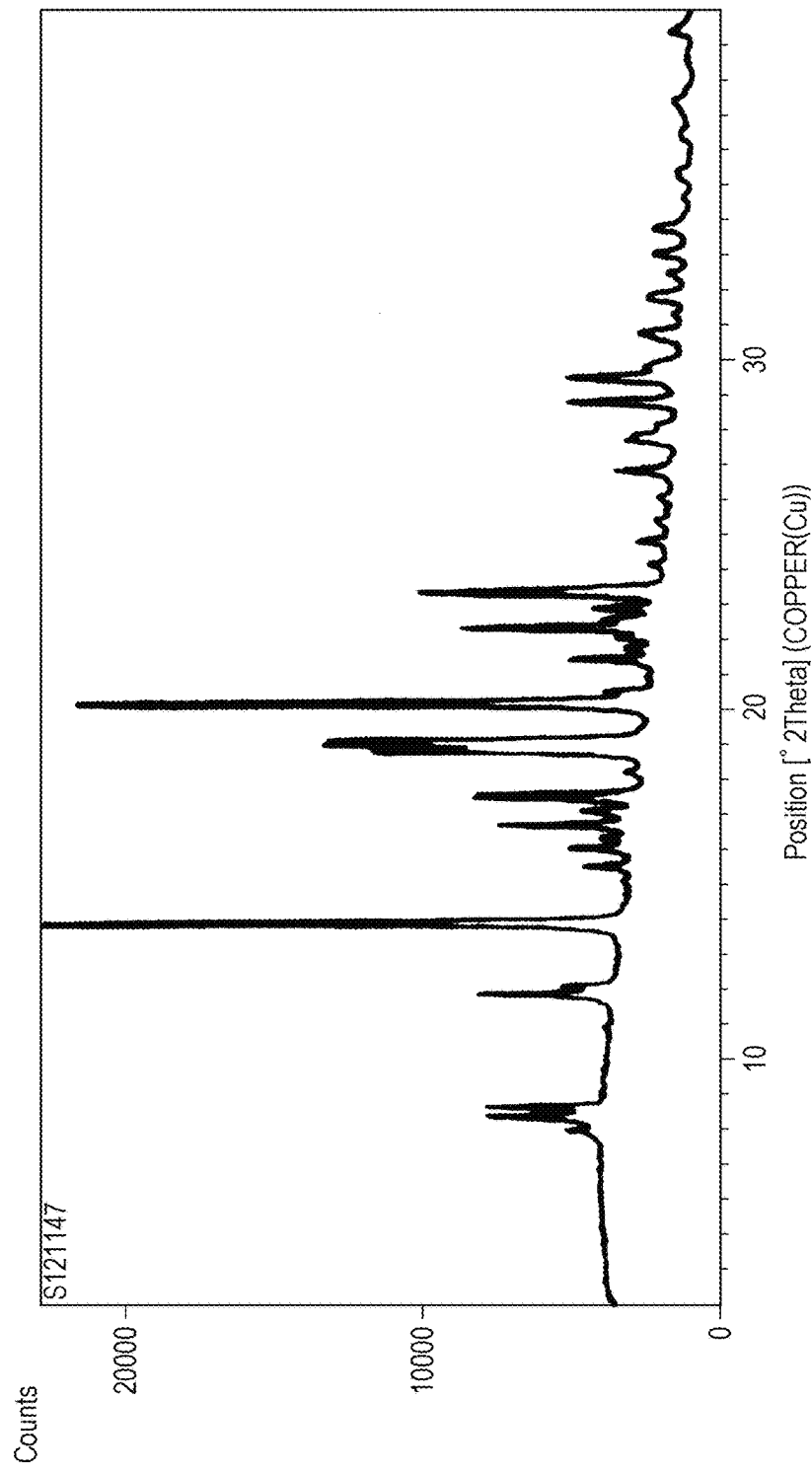
FIG. 2 is a graph showing a result of X-ray powder diffraction measurement on form I crystals.

The form I crystals are characterized by having an X-ray powder diffraction pattern with peaks at diffraction angles (2θ) of 8.4°, 14.0°, 16.7°, 18.8°, and 23.3°. An example of a result of X-ray powder diffraction measurement on the form I crystals is shown in FIG. 2, and examples of peaks in X-ray powder diffraction patterns of these crystals are shown in Table 1. The form I crystals can be obtained by adding a solution containing the compound of the formula (I) dropwise to a liquid mixture of ethanol and hydrochloric acid, which contains 1 molar equivalent or more of hydrochloric acid relative to the compound of the formula (I), while keeping the temperature of the liquid mixture at about 35° C. or higher.

TABLE 1

| Diffraction angle (2θ) | | |
|---|---|---|
| 3.5 | 20.2 | 28.8 |
| 8.0 | 20.5 | 29.5 |
| 8.4 | 21.0 | 29.9 |
| 8.7 | 21.5 | 30.8 |
| 11.0 | 21.8 | 31.3 |
| 11.9 | 22.1 | 31.8 |
| 12.1 | 22.3 | 31.9 |
| 14.0 | 22.6 | 32.6 |
| 15.1 | 22.9 | 33.1 |
| 15.6 | 23.3 | 33.2 |
| 16.1 | 24.1 | 33.8 |
| 16.4 | 24.8 | 34.7 |
| 16.7 | 25.4 | 35.3 |
| 17.1 | 25.7 | 35.5 |
| 17.5 | 26.1 | 36.4 |
| 18.2 | 26.9 | 36.6 |
| 18.8 | 27.7 | 37.5 |
| 19.0 | 27.9 | 38.8 |
| 19.1 | 28.2 | 39.4 |

Figure 3:
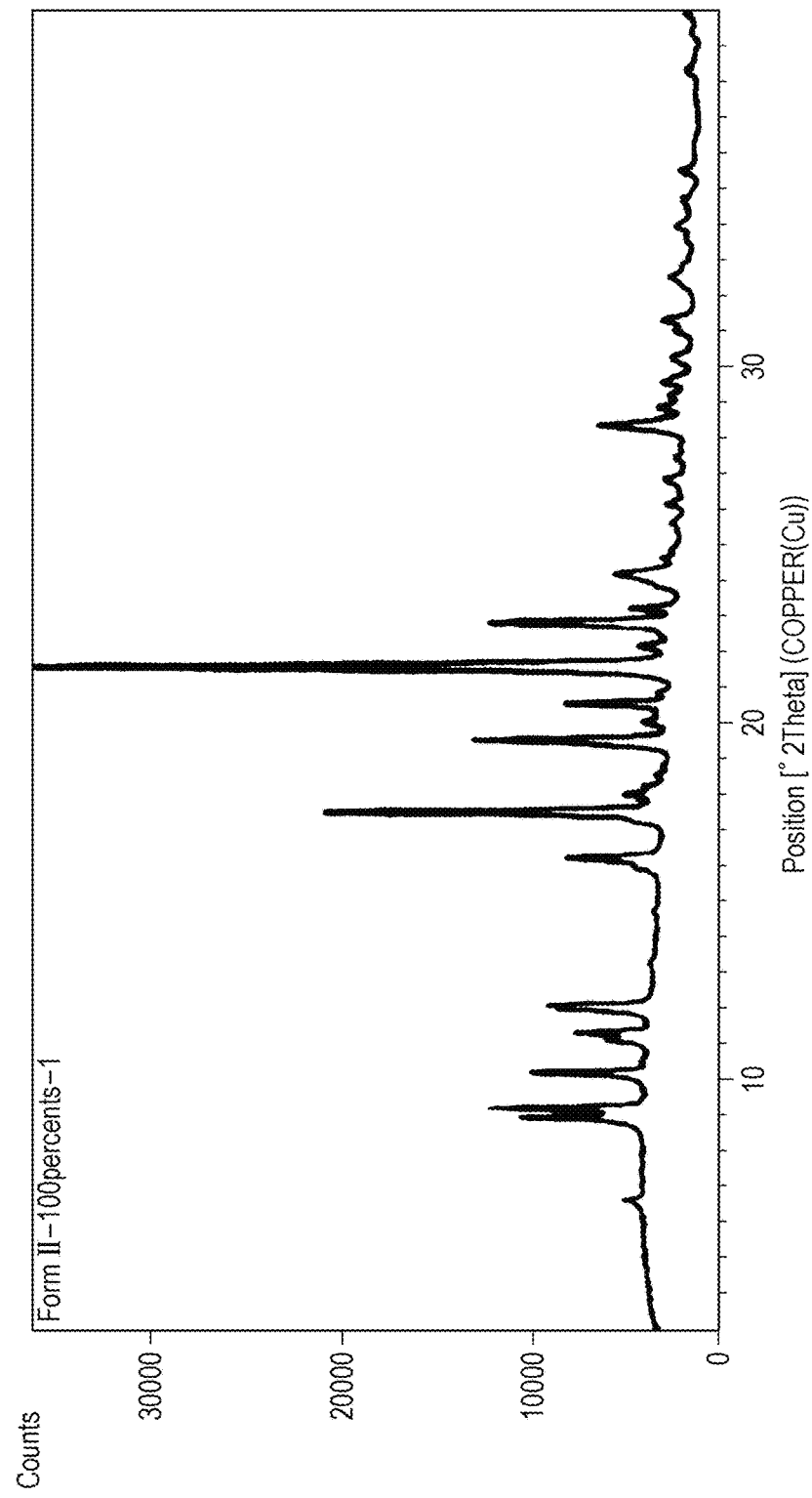
FIG. 3 is a graph showing a result of X-ray powder diffraction measurement on form II crystals.

The form II crystals are characterized by having an X-ray powder diffraction pattern with peaks at diffraction angles (2θ) of 9.2°, 10.2°, 16.2°, 20.5°, and 21.6°, and more specifically at diffraction angles (2θ) of 9.2°, 10.2°, 16.2°, 17.5°, 19.5°, 20.5°, 21.6°, and 22.8°. An example of a result of X-ray powder diffraction measurement on the form II crystals is shown in FIG. 3, and examples of peaks in X-ray powder diffraction patterns of these crystals are shown in Table 2. The form II crystals can be obtained by drying form III crystals described later at about 40° C. under reduced pressure.

TABLE 2

| Diffraction angle (2θ) | | |
|---|---|---|
| 3.6 | 19.5 | 29.2 |
| 6.6 | 20.0 | 29.6 |

TABLE 2-continued

| Diffraction angle (2θ) | | |
|---|---|---|
| 8.9 | 20.5 | 30.3 |
| 9.2 | 20.8 | 31.0 |
| 10.2 | 21.6 | 31.3 |
| 11.1 | 22.2 | 32.6 |
| 11.3 | 22.8 | 32.9 |
| 12.0 | 23.2 | 33.6 |
| 12.1 | 23.8 | 34.0 |
| 13.3 | 24.2 | 34.8 |
| 14.6 | 24.6 | 35.5 |
| 16.0 | 24.8 | 36.2 |
| 16.2 | 25.6 | 37.7 |
| 17.3 | 26.2 | 38.3 |
| 17.5 | 26.9 | 38.8 |
| 18.0 | 27.5 | 39.4 |
| 18.2 | 27.8 | 39.9 |
| 18.5 | 28.4 | |
| 18.8 | 28.9 | |

In one embodiment of the present invention, the form II crystals are monohydrate. The monohydrate herein is not specifically limited as long as it is a crystal that stably contains about 1 equivalent of water under environments (e.g., temperature and relative humidity) where drugs are generally stored and used.

Figure 4:
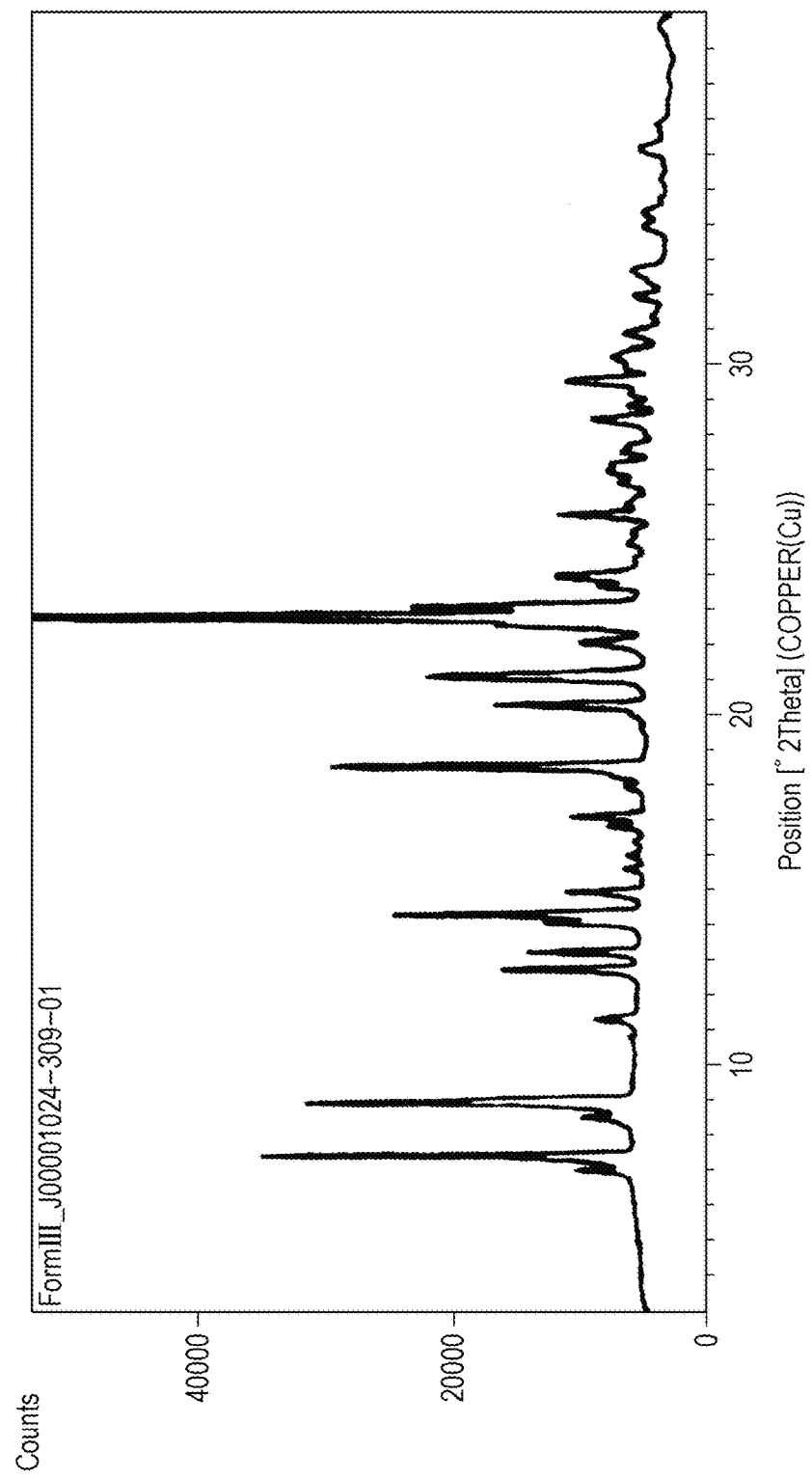
FIG. 4 is a graph showing a result of X-ray powder diffraction measurement on form III crystals.

The form III crystals can be obtained by adding a solution containing the compound of the formula (I) dropwise to a liquid mixture of ethanol and hydrochloric acid, which contains 1 molar equivalent or more of hydrochloric acid relative to the compound of the formula (I), while keeping the temperature of the liquid mixture at about 15° C. The form III crystals are characterized by having an X-ray powder diffraction pattern with peaks at diffraction angles (2θ) of 12.7°, 14.3°, 15.0°, 18.5°, and 25.7°, and more specifically at diffraction angles (2θ) of 7.5°, 12.7°, 14.3°, 15.0°, 18.5°, 20.3°, 21.0°, and 25.7°. FIG. 4 shows an example of a result of X-ray powder diffraction measurement on the form III crystals, and Table 3 shows examples of peaks in X-ray powder diffraction patterns of these crystals.

TABLE 3

| Diffraction angle (2θ) | | |
|---|---|---|
| 3.5 | 19.9 | 29.5 |
| 7.0 | 20.3 | 29.6 |
| 7.5 | 21.0 | 29.9 |
| 8.5 | 22.1 | 30.3 |
| 9.0 | 22.5 | 30.5 |
| 10.8 | 22.8 | 30.9 |
| 11.3 | 23.1 | 31.4 |
| 11.4 | 23.7 | 32.1 |
| 12.7 | 24.0 | 32.8 |
| 13.3 | 24.5 | 34.0 |
| 14.1 | 24.9 | 34.4 |
| 14.3 | 25.2 | 34.8 |
| 15.0 | 25.7 | 35.3 |
| 15.7 | 26.0 | 36.2 |
| 16.0 | 26.7 | 36.3 |
| 16.4 | 26.9 | 36.7 |
| 16.8 | 27.2 | 36.9 |
| 17.1 | 27.5 | 37.6 |
| 17.9 | 27.7 | 38.2 |
| 18.2 | 28.5 | |
| 18.5 | 28.8 | |
| 19.6 | 29.1 | |

The analysis of crystalline forms using X-ray powder diffraction can be performed according to a method usually used such as the "X-ray powder diffraction method" described in, for example, Japanese Pharmacopoeia (16th edition). The same crystal form typically refers to crystalline forms of which diffraction angles 2θ coincide with each other with an error of ±0.2°.

An example of measurement conditions for an X-ray powder diffraction analysis is given below.

Measuring instrument: X'Pert-Pro MPD (manufactured by PANalytical)
Target: Cu
Tube voltage: 45 kV
Tube current: 40 mA
Step size: 0.02
Scan axis: 2θ
Sampling time per step: 43 sec.
Scanning range: 3 to 40°

Water content of the crystals can be measured using a method usually used: for example, with a dynamic vapor sorption instrument or by the Karl Fischer method.

An example of measurement conditions for a dynamic vapor sorption instrument is given below.

Dynamic vapor sorption instrument: DVS-1 (Surface Measurement Systems)
Temperature: fixed temperature about 25° C.
Atmospheric gas: dried nitrogen
Flow rate of atmospheric gas: 200 sccm (mL/min.)
Minimum equilibration time: 10 min.
Maximum equilibration time: 1200 min.

An example of measurement conditions for the measurement of water content using a Karl Fischer analyzer is given below.

Method of analysis: coulometric, titration method
KF analyzer: volumetric moisture meter, model KF-100 (manufactured by Mitsubishi Chemical Corporation)
Anode solution: Aquamicron AX (manufactured by Mitsubishi Chemical Corporation)
Cathode solution: Aquamicron CXU (manufactured by Mitsubishi Chemical Corporation)

Examples of the salts of the compound represented by the formula (I) in the present invention include hydrochlorides, hydrobromides, hydroiodides, phosphates, phosphonates, sulfates, and sulfonates such as methanesulfonates and p-toluenesulfonates, carboxylates such as acetates, citrates, malates, tartrates, succinates, and salicylates, or alkali metal salts such as sodium salts and potassium salts; alkaline earth metal salts such as magnesium salts and calcium salts; and ammonium salts such as ammonium salts, alkylammonium salts, dialkylammonium salts, trialkylammonium salts, and tetraalkylammonium salts. These salts are produced by contacting the compound with an acid or a base that can be used for the production of drugs.

A solvate of the compound represented by the formula (I) or a salt thereof can be either hydrate or non-hydrate. Examples of non-hydrates of the compound represented by the formula (I) or salts thereof include their solvates with alcohol (e.g., methanol, ethanol, and n-propanol), or dimethylformamide.

The amorphous forms of the present invention have an excellent solubility and are thus expected to exhibit better absorbability in living bodies, in particular, higher intestinal absorbability than conventional crystalline forms. Accordingly, by using an amorphous form of the present invention in place of a crystalline form of the compound represented by the formula (I) or a salt thereof; a daily dose can be reduced. It is useful as drugs and medicines, in particular, oral pharmaceutical formulations.

Although typical amorphous forms crystallize fast and may sometimes have a problem in stability, the amorphous forms of the present invention hardly undergo crystallization and are thus stable. The amorphous forms of the present invention which are thus superior in stability are advantageous in terms of manufacturing and providing as well as using the products with a certain level of quality as drugs.

The amorphous forms of the present invention can be manufactured using spray drying.

The "spray drying" is a method of producing a dry powder of a compound by atomizing a solution, slurry, or emulsion containing the compound, which is referred to as a "feed solution", to fine droplets and injecting them into a hot air stream. Injection of mist is also referred to as "spraying" and as a method for this, centrifugal spraying using a rotary disk and pressure spraying using a pressure nozzle are well known.

Spray drying can be performed according to a method usually used. With spray drying, it is possible to produce stable and uniform amorphous forms with a high reproducibility, which is advantageous in terms of manufacturing and providing products with a certain level of quality as drugs.

Examples of the aforementioned spray drying include a production method including the steps of: dissolving the compound represented by the general formula (I):

[Chemical Formula 2]

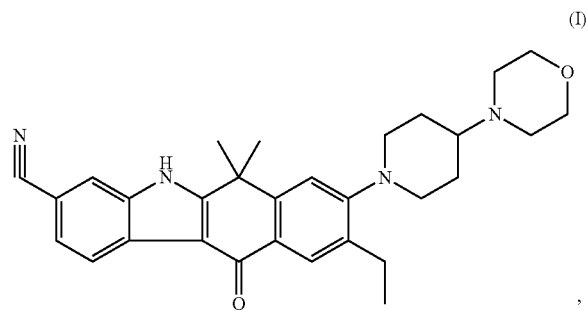

(I)

a salt thereof or a solvate of the compound or a salt thereof into a solvent to prepare a feed solution; spraying the feed solution; and drying the sprayed feed solution to give an amorphous form thereof.

One embodiment of the step of preparing the feed solution is to prepare it by dissolving form I crystals of monohydrochloride of the compound represented by the formula (I) into a solvent.

Solvents used for the spray drying include tetrahydrofuran. The concentration of tetrahydrofuran is, for example, 65% to 85%, and about 70% is preferable.

The temperature at which the compound represented by the formula (I), a salt thereof, or a solvate of the compound or a salt thereof is dissolved into a solvent is preferably about 50° C. (±5° C.).

The temperature during the spray drying is preferably about 120° C. (±5° C.).

If a sample obtained by spray drying contains a residual solvent, a step of removing the solvent, such as a step of drying the sample under reduced pressure, can be included as a post-processing.

Furthermore, the present invention also relates to solid dispersions containing an amorphous form of the compound represented by the formula (I), a salt thereof, or a solvate of the compound or a salt thereof; and an inert carrier. Since the amorphous form of the compound represented by the formula (I), a salt thereof, or a solvate of the compound or a salt thereof is stabilized more in the solid dispersion, its storage stability is improved and thus it is useful for actual clinical practices.

The "solid dispersion" as used in the present invention refers to a solid composition in which one or more active ingredients are dispersed in an inert carrier or a matrix thereof. In the solid dispersion of the present invention, the active ingredient is preferably dispersed in the inert carrier or a matrix thereof at a molecular level.

The "inert carrier" as used in the present invention means a solid or liquid vehicle diluent and may contain a plurality of substances. Preferable examples of the inert carrier include solid polymers. Solid polymers are not specifically limited as long as they are pharmaceutically acceptable and can keep an amorphous state of the active ingredient(s). One of the solid polymers alone or a mixture of two or more can be used. A weight ratio of the amorphous form of the compound represented by the formula (I), a salt thereof, or a solvate of the compound or a salt thereof, as a free form, to the inert carrier is, for example, 9:1 to 1:9, preferably 2:1 to 1:9, and more preferably 1:2 to 1:9.

A preferable embodiment of the present invention includes a solid dispersion in which an amorphous form of the compound represented by formula (I), a salt thereof, or a solvate of the compound or a salt thereof is dispersed in a solid polymer. A more preferable embodiment includes a solid dispersion in which the amorphous form is dispersed in the solid polymer at a molecular level.

Examples of the solid polymer include celluloses and their derivatives, and water-soluble synthetic polymers.

Examples of celluloses and their derivatives include hypromellose, hypromellose acetate succinate, hypromellose phthalate, carboxymethyl cellulose, carboxymethyl ethyl cellulose, sodium carboxymethyl cellulose, hydroxyethyl cellulose, hydroxyethyl methyl cellulose, hydroxypropyl cellulose, methyl cellulose, ethyl cellulose, and cellulose acetate phthalate. Among the aforementioned solid polymers, preferable examples include hypromellose acetate succinate and hypromellose phthalate.

Examples of water-soluble synthetic polymers include polyethylene glycol, polyvinyl alcohol, povidone, copolyvidone, polyvinyl acetate phthalate, polyvinylacetal diethylamino acetate, cellulose acetate phthalate, a polyvinyl caprolactam-polyvinyl acetate-polyethylene glycol graft copolymer (product name: Soluplus), an aminoalkyl methacrylate copolymer E, an aminoalkyl methacrylate copolymer RS, a methacrylate copolymer L, a methacrylate copolymer LD, a methacrylate copolymer S, and carboxyvinyl polymers. Among the aforementioned solid polymers, preferable examples include the polyvinyl caprolactam-polyvinyl acetate-polyethylene glycol graft copolymer and the methacrylate copolymer L.

These solid dispersions can be obtained preferably by spray drying. Specifically, it can be obtained by, for example, dissolving the compound represented by the formula (I), a salt thereof, or a solvate of the compound or a salt thereof and other solid substance (such as the solid polymer) in a solvent, spray drying the solution thus obtained at about 100° C., and optionally, drying under reduced pressure as a post-processing.

The weight ratio of the solid polymer to the amorphous form of the compound represented by the formula (I), a salt thereof, or a solvate of the compound or a salt thereof, as a free form, is, for example, 9:1 to 1:9, preferably 2:1 to 1:9, and more preferably 1:2 to 1:9.

The amorphous forms of the present invention can be administered orally or parenterally. As oral dosage forms, powders, fine granules, granules, tables, and capsules are suitably used. As parenteral dosage forms, suppositories and the like are suitably used. When the amorphous form of the present invention is used as a solid dispersion, the solid dispersion itself can be used as a pharmaceutical preparation. It can also be used as a pharmaceutical preparation in the form of powders, fine granules, granules, tables, or capsules using a formulation technique such as compression molding. The amorphous forms, the solid dispersions and the pharmaceutical preparations of the present invention can be used for a liquid medicine in which they have been dispersed in a pharmaceutically acceptable solution in advance. In such a case, they can be used for syrups for oral administration or injections for parenteral administration which includes a lyophilized agent for injection to be used after being reconstituted. They can also be prepared for liposomal drugs.

For preparation of the dosage forms, a coloring agent, a sweetening agent, and a flavor, usually used; a diluent, an excipient, a binder, a lubricant, a disintegrating agent, a softening agent, a suspending agent, an emulsifying agent, a preservative, an antioxidant, a surfactant, a stabilizing agent, a pH adjusting agent, and a dispersing agent can be used. These various dosage forms may be prepared according to a method usually used, and may be prepared aseptically.

For example, the disintegrating agent can be starches such as corn starches, potato starches, and partially pregelatinized starches, celluloses such as crystalline celluloses and microcrystalline celluloses, low-substituted hydroxypropyl celluloses, croscarmellose sodium, crospovidone, carmellose calcium, carmellose sodium, and carboxymethyl starch sodium.

As the excipients, examples include sugars such as lactose, sucrose, glucose, reducing maltose, mannitol, sorbitol, and erythritol, starches and their derivatives such as corn starches, potato starches, pregelatinized starches, partially pregelatinized starches, dextrin, and pullulan, celluloses such as crystalline celluloses and microcrystalline celluloses, magnesium silicate, magnesium aluminate metasilicate, sodium hydrogen phosphate, calcium hydrogen phosphate, and talc.

Examples of the lubricants include carnauba waxes, hydrogenated oils, stearic acid, magnesium stearate, calcium stearate, talc, sodium stearyl fumarate, and sucrose fatty acid ester.

Furthermore, the solid dispersion or the pharmaceutical preparation of the present invention may partly contain crystals of the compound represented by the formula (I), a salt thereof, or a solvate of the compound or a salt thereof. Preferably, at least 75% of the compound represented by the formula (I), a salt thereof, or a solvate of the compound or a salt thereof in the solid dispersion or the pharmaceutical preparation is present in the amorphous form, but not limited thereto. More preferably, this amount is at least 90%, and yet more preferably, 95%. The percentage of the amorphous forms can be obtained by comparing spectra of the X-ray powder diffraction between the crystalline and amorphous forms.

Exemplified formulations of pharmaceutical preparations containing form I crystals of a monohydrochloride of the compound represented by the formula (I) as an active ingredient are shown in Table 4. These pharmaceutical preparations can be produced using the following method.

Ingredients to be formulated as granules are loaded and premixed in a high-shear granulator. An appropriate amount of purified water is sprayed and the ingredients are agitated and granulated. They are then dried under vacuum to give dry granules. The dry granules are sized using a sizing machine. The sized granules thus obtained and ingredients externally added are mixed in a mixer to produce mixed powders. The mixed powders are filled in a capsule to produce a capsule drug.

The pharmaceutical preparation can contain 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% by weight or less of the amorphous form of the present invention relative to the entire monohydrochloride of the compound of the formula (I) contained in the pharmaceutical preparation.

TABLE 4

| | Name | Preparation 1 | Preparation 2 |
|---|---|---|---|
| Ingredients to be formulated as granules | Hydrochloride of the compound of formula (I) | 161.33 | 161.33 |
| | Lactose monohydrate | 33.67 | 52.42 |
| | Hydroxypropyl cellulose | 15.00 | 15.00 |
| | Sodium lauryl sulfate | 75.00 | 56.25 |
| | Carmellose calcium | 15.00 | 0.00 |
| | Low-substituted hydroxypropyl cellulose | 0.00 | 15.00 |
| Ingredients externally added | Carmellose calcium | 28.35 | 0.00 |
| | Low-substituted hydroxypropyl cellulose | 0.00 | 28.35 |
| | Magnesium stearate | 1.65 | 1.65 |
| Total | | 330.00 | 330.00 |

In the present specification, the following abbreviations may be used.

MeOH: methanol

EtOH: ethanol

MeCN: acetonitrile

THF: tetrahydrofran

EtOAc: ethyl acetate

DMSO: dimethyl sulfoxide tBuOH: tert-butyl alcohol

EXAMPLES

The present invention is described specifically with reference to the Examples but they are merely exemplified and the present invention is not limited thereto.

Reference Example 1

Form I Crystals of 9-ethyl-6,6-dimethyl-8-(4-morpholin-4-yl-piperidin-1-yl)-11-oxo-6,11-dihydro-5H-benzo[b]carbazole-3-carbonitrilemonohydrochloride 400 g of 9-ethyl-6,6-dimethyl-8-(4-morpholin-4-yl-piperidin-1-yl)-11-oxo-6,11-dihydro-5H-benzo[b]carbazole-3-carbonitrile was dissolved in a mixed solvent of 4.8 L of methyl ethyl ketone, 1.44 L of acetic acid, and 1.68 L of distilled water at room temperature, and the solution was added dropwise to a mixture of 12 L of ethanol and 0.8 L of 2N hydrochloric acid at 60° C. Precipitated solids were recovered by filtration, washed with 2 L of ethanol, and dried to give 357 g of form I crystals of a monohydrochloride of the title compound.

Reference Example 2

Form III Crystals of 9-ethyl-6,6-dimethyl-8-(4-morpholin-4-yl-piperidin-1-yl)-11-oxo-6,11-dihydro-5H-benzo[b]carbazole-3-carbonitrilemonohydrochloride 9-ethyl-6,6-dimethyl-8-(4-morpholin-4-yl-piperidin-1-yl)-11-oxo-6,11-dihydro-5H-benzo[b]carbazole-3-carbonitrile (9.00 g) was dissolved in a mixed solvent of methyl ethyl ketone (90 ml), distilled water (31.5 ml), and acetic acid (27.0 ml). This solution was added dropwise to a liquid mixture of ethanol (90 ml) and 2N hydrochloric acid (18.00 ml) stirred at 15° C. while keeping the temperature of the liquid mixture at 15° C. Subsequently, it was washed with a mixed solvent of methyl ethyl ketone (18.00 ml), distilled water (6.30 ml), and acetic acid (5.40 ml) and then stirred at 15° C. Precipitated solids were recovered by filtration to give form III crystals of a monohydrochloride of the title compound.

Reference Example 3

Form II Crystals of 9-ethyl-6,6-dimethyl-8-(4-morpholin-4-yl-piperidin-1-yl)-11-oxo-6,11-dihydro-5H-benzo[b]carbazole-3-carbonitrilemonohydrochloride The form III crystals obtained in Reference example 2 were washed with ethanol (90 ml) and then dried under reduced pressure at 40° C. for about 16 hours to give form II crystals of a monohydrochloride of the title compound.

Reference Example 4

Form II Crystals of 9-ethyl-6,6-dimethyl-8-(4-morpholin-4-yl-piperidin-1-yl)-11-oxo-6,11-dihydro-5H-benzo[b]carbazole-3-carbonitrilemonohydrochloride 9-ethyl-6,6-dimethyl-8-(4-morpholin-4-yl-piperidin-1-yl)-11-oxo-6,11-dihydro-5H-benzo[b]carbazole-3-carbonitrile (4.00 g) was added to a mixed solvent of methyl ethyl ketone (40 ml), distilled water (14 ml), and acetic acid (12 ml) and dissolved therein at 35° C. This solution was added dropwise to a liquid mixture of ethanol (40 ml) and 2N hydrochloric acid (8.00 ml) (stirred at 15° C.) while keeping the temperature of the liquid mixture at 15° C. To this liquid mixture, a mixed solvent of methyl ethyl ketone (8.00 ml), distilled water (2.80 ml), and acetic acid (2.40 ml) was added dropwise while keeping the temperature of the liquid mixture at 15° C. Subsequently, the liquid mixture was stirred at 15° C. Precipitated solids were recovered by filtration, washed with ethanol (40 ml) and then dried under reduced pressure at 40° C. to give form II crystals (2.4805 g) of a monohydrochloride of the title compound.

Reference Example 5

Form III Crystals of 9-ethyl-6,6-dimethyl-8-(4-morpholin-4-yl-piperidin-1-yl)-11-oxo-6,11-dihydro-5H-benzo[b]carbazole-3-carbonitrilemonohydrochloride 9-ethyl-6,6-dimethyl-8-(4-morpholin-4-yl-piperidin-1-yl)-11-oxo-6,11-dihydro-5H-benzo[b]carbazole-3-carbonitrile (4.00 g) was added to a mixed solvent of methyl ethyl ketone (40 ml), distilled water (14 ml), and acetic acid (12 ml) and dissolved therein at 35° C. This solution was added dropwise to a liquid mixture of ethanol (40 ml) and 2N hydrochloric acid (8.00 ml) (stirred at 15° C.) while keeping the temperature of the liquid mixture at 15° C. A mixed solvent of methyl ethyl ketone (8.00 ml), distilled water (2.80 ml), and acetic acid (2.40 ml) was added dropwise while keeping the temperature of the liquid mixture at 15° C. Subsequently, the liquid mixture was stirred at 15° C. Precipitated solids were recovered by filtration to give form III crystals (7.8435 g) of monohydrochloride of the title compound.

X-Ray Powder Diffraction Analysis

X-ray powder diffraction was measured under the following conditions on form I, II, and III crystals of 9-ethyl-6,6-dimethyl-8-(4-morpholin-4-yl-piperidin-1-yl)-11-oxo-6,11-dihydro-5H-benzo[b]carbazole-3-carbonitrilemonohydrochloride obtained in Reference examples 1 to 5. Results of the measurement on the form II, III, and I crystals are shown in FIGS. 2 to 4.

Measuring instrument: X'Pert-Pro MPD (manufactured by PANalytical)
Target: Cu
Tube voltage: 45 kV
Tube current: 40 mA
Step size: 0.02
Scan axis: 2θ
Sampling time per step: 43 sec.
Scanning range: 3 to 40°

[Example 1] Preparation of an Amorphous Form of Hydrochloride of the Compound of the Formula (I)

A mixed solvent (40 mL) of tetrahydrofuran (140 mL) and water (60 mL) was added to a vessel containing form I crystals (600 mg) of monohydrochloride of 9-ethyl-6,6-dimethyl-8-(4-morpholin-4-yl-piperidin-1-yl)-11-oxo-6,11-dihydro-5H-benzo[b]carbazole-3-carbonitrile and the vessel was warmed in a water bath at 50° C. Subsequently, the mixture was stirred until the salt was dissolved. The solution thus obtained was spray-dried at about 120° C. and dried under reduced pressure as a post-processing to give an amorphous form (530 mg) of monohydrochloride of the title compound.

Conditions during the spray-drying are as follows.
Spraying pressure 20-30 mbar
Inlet temperature: 120° C.

[Test Example 1] X-Ray Powder Diffraction Analysis

X-ray powder diffraction was measured under the following conditions on the amorphous form of 9-ethyl-6,6-dimethyl-8-(4-morpholin-4-yl-piperidin-1-yl)-11-oxo-6,11-dihydro-5H-benzo[b]carbazole-3-carbonitrilemonohydrochloride obtained in Example 1. A result of measurement is shown in FIG. 1.

Measuring instrument: X'Pert-Pro MPD (manufactured by PANalytical)
Target: Cu
Tube voltage: 45 kV
Tube current: 40 mA
Step size: 0.02°
Scan axis: 2θ
Sampling time per step: 43 sec.
Scanning range: 3 to 40°

The amorphous form obtained in Example 1 had an X-ray powder diffraction pattern with a halo pattern, confirming that it is an amorphous form.

[Test Example 2] Differential Scanning Calorimetry (DSC)

Figure 5:
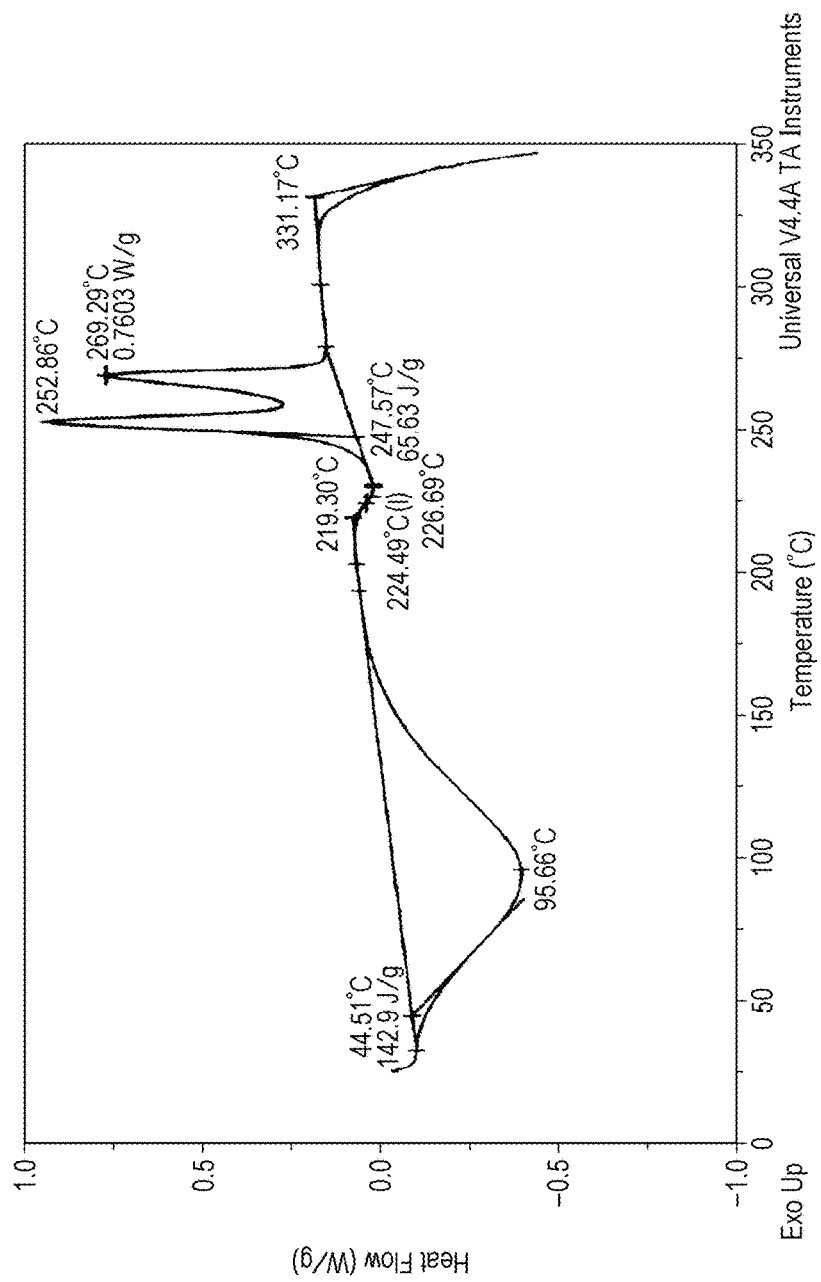
FIG. 5 is a graph showing a result of differential scanning calorimetry (DSC) measurement on the amorphous form of the present invention.

Differential scanning calorimetry was performed under the following conditions on the amorphous form of 9-ethyl-6,6-dimethyl-8-(4-morpholin-4-yl-piperidin-1-yl)-11-oxo-6,11-dihydro-5H-benzo[b]carbazole-3-carbonitrilemonohydrochloride obtained in a manner similar to Example 1. A result is shown in FIG. 5. Two exothermic peaks (at 252.86° C. and 269.29° C.) were observed. Furthermore, after the exothermic change, the samples were removed at about 300° C. and stored at room temperature. Then, X-ray powder diffraction analysis was performed and as a result, it was found that transformation from the amorphous form to the crystalline form had occurred. The glass transition temperature was found at about 224.5° C.

Name of instrument: differential scanning calorimeter (DSC)
Model: Q200 (manufactured by TA Instruments)
Heating rate: 10° C./min.
Measurement temperature range: 25° C. to 350° C.
Atmospheric gas: dried nitrogen
Flow rate of atmospheric gas: 50 mL/min.
Cell: aluminum pan (pinhole)
Sample volume: 5 mg to 10 mg
Reference standard: empty pan

[Example 2] Comparison of Solvents to Obtain Amorphous

Solubility of 9-ethyl-6,6-dimethyl-8-(4-morpholin-4-yl-piperidin-1-yl)-11-oxo-6,11-dihydro-5H-benzo[b]carbazole-3-carbonitrilemonohydrochloride (hereinafter, a compound A) to each solvent was evaluated.

5 mL of each of the solvents described in Table 5 was added to 5 mg of form I crystals of the compound A. When undissolved crystals were observed, the mixture was stirred at room temperature and the crystals were dissolved using ultrasound (step 1). After the processing described, when undissolved crystals were observed the mixture was further stirred in a water bath at about 50° C. (step 2).

When the crystals were dissolved completely, the form I crystals of the compound A were further added (step 3).

The procedure of the steps 1 to 3 was repeated.

For $CH_2Cl_2$, the step 2 and the later step were performed at room temperature.

Results obtained for the solvent other than THF are given in Table 6, and results obtained for THF are given in Table 7.

TABLE 5

| | | Solvent used | | | |
|---|---|---|---|---|---|
| | | Water content (v/v) | | | |
| | | 0% | 10% | 20% | 30% |
| Solvent | MeOH | NA | NA | NA | X |
| | EtOH | NA | NA | NA | X |
| | Acetone | NA | NA | NA | X |
| | MeCN | NA | NA | NA | X |
| | THF | X | X | X | X |
| | EtOAC | X | NA | NA | NA |
| | $CH_2Cl_2$ | X | NA | NA | NA |
| | DMSO | X | | | |
| | tBuOH | X | | | |
| | Dioxane | X | | | |

NA: not assessed
X: assessed

TABLE 6

| | | Concentration of the compound A in solvent | | | | | |
|---|---|---|---|---|---|---|---|
| | | 1 mg/mL | 2 mg/mL | 4 mg/mL | 6 mg/mL | 8 mg/mL | 10 mg/mL |
| Solvent | 70% MeOH | Y/— | Y/— | N/Y | — | — | — |
| | 70% EtOH | Y/— | Y/— | Y/— | N/Y | — | — |
| | 70% acetone | Y/— | Y/— | Y/— | Y/— | N/Y | — |
| | 70% MeCN | Y/— | Y/— | Y/— | Y/— | Y/— | N/Y* |
| | EtOAc | N/N | — | — | — | — | — |
| | CH2Cl2 | N/— | — | — | — | — | — |
| | DMSO | Y/— | Y/— | N/Y | — | — | — |
| | t-BuOH | N/N | — | — | — | — | — |
| | 1,4-dioxane | N/N | — | — | — | — | — |

The results obtained at room temperature are shown on the left side of "/" and the results obtained at about 50° C. while stirring are shown on the right side thereof.
Results:
Y: dissolved,
N: not dissolved,
—: not tested
*Formation of solids was observed inside the test tube.

TABLE 7

| | | Concentration of the compound A (mg/mL) | | | | | | | | |
|---|---|---|---|---|---|---|---|---|---|---|
| | | 1 | 2 | 3 | 4 | 5 | 6 | 8 | 10 | 12 | 14 |
| Concentration of THF | 100% | N/N | — | — | — | — | — | — | — | — | — |
| | 90% | Y/— | — | Y/— | — | N/N | — | — | — | — | — |

TABLE 7-continued

| | Concentration of the compound A (mg/mL) | | | | | | | | | |
|---|---|---|---|---|---|---|---|---|---|---|
| | 1 | 2 | 3 | 4 | 5 | 6 | 8 | 10 | 12 | 14 |
| 80% | Y/— | — | — | Y/— | — | Y/— | Y/— | Y/— | Y/— | — |
| 70% | Y/— | — | — | — | — | Y/— | Y/— | Y/— | Y/— | Y/— |

The results obtained at room temperature are shown on the left side of "/" and the results obtained at about 50° C. while stirring are shown on the right side thereof.
Results:
Y: dissolved,
N: not dissolved,
—: not tested

[Example 3] Examination Using Polarizing Microscope

Figure 6:
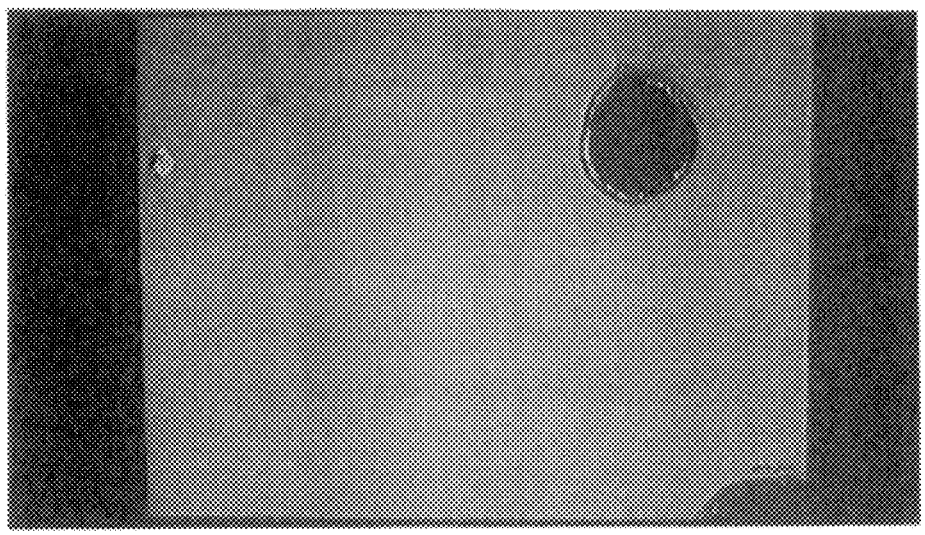
FIG. 6 shows a polarizing micrograph of a compound A which has been dried after being completely dissolved in 70% THF (concentration of the compound A: 14 mg/mL).
Figure 7:
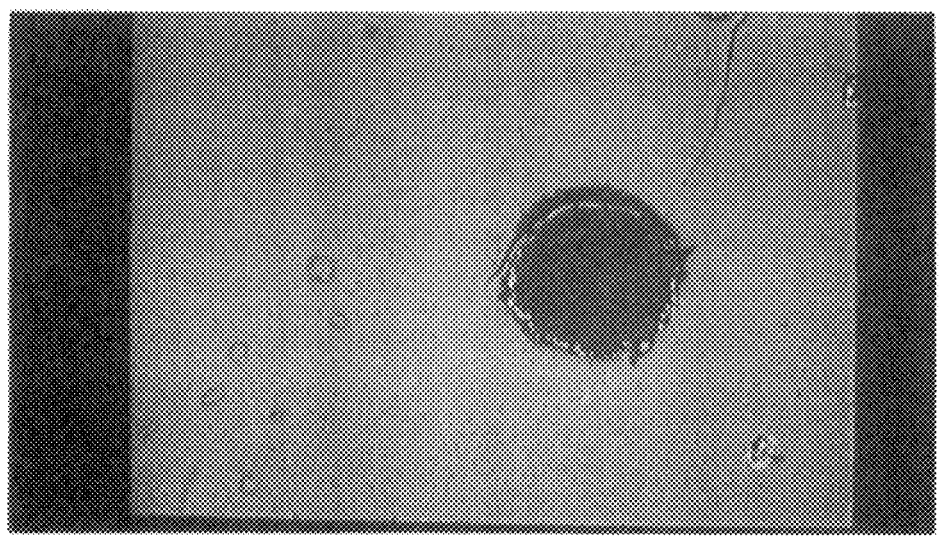
FIG. 7 shows a polarizing micrograph of the compound A which has been dried after being completely dissolved in 80% THF (concentration of the compound A: 12 mg/mL).

Among the solutions obtained in Example 2, those in which the form I crystals of the compound A were found to be dissolved were dried on glass dishes placed on a hot plate heated at 100° C. or higher. The solids thus obtained were examined using a polarizing microscope. Results are shown in FIGS. 6 and 7. It was determined that amorphous forms could be obtained when 70% THF (in which the concentration of the compound A is 14 mg/mL) and 80% THF (in which the concentration of the compound A is 12 mg/mL) were used (see, FIGS. 6 and 7).
(Reference)
It was observed that when the form I crystals of monohydrochloride of the compound represented by the formula (I) were pulverized using a jet mill, a small amount of amorphous form was formed in crystals, but the amorphous form tended to crystallize soon.

[Example 4] Stability Test

The amorphous form of 9-ethyl-6,6-dimethyl-8-(4-morpholin-4-yl-piperidin-1-yl)-11-oxo-6,11-dihydro-5H-benzo[b]carbazole-3-carbonitrilemonohydrochloride was stored under a certain condition and transition of the state of the amorphous form of the test compound was analyzed using. X-ray power diffraction as in the Test example 1. Results are shown in Table 8. As a result, it was found in a long-term stability test of 12 months under conditions of 30° C. and 75% RH and in an accelerated test of 6 months under conditions of 40° C. and 75% RH that the amorphous form hardly crystallized and physically stable, when it was stored in a sealed condition.

TABLE 8

| Storage temperature/ | | Storage period (month) | | | |
|---|---|---|---|---|---|
| humidity (° C./% RH) | Storage state | 1 | 3 | 6 | 12 |
| 25/93 | Open | X | X | X | — |
| 30/75 | Sealed | — | ○ | ○ | ○ |
| 40/75 | Sealed | ○ | ○ | ○ | — |

○: no peak of diffraction angle,
X: clear peak of diffraction angle,
—: not measured Example 5

A test of measuring intrinsic dissolution rate (according to USP chapter 1087 "APPARENT INTRINSIC DISSOLUTION-DISSOLUTION TESTING PROCEDURES FOR ROTATING DISK AND STATIONARY DISK") was performed on a composition containing the amorphous and crystalline forms (form I crystals) of 9-ethyl-6,6-dimethyl-8-(4-morpholin-4-yl-piperidin-1-yl)-11-oxo-6,11-dihydro-5H-benzo[b]carbazole-3-carbonitrilemonohydrochloride at certain ratios. Results are shown in Table 9. It was concluded that the dissolution rate was increased when the content of the amorphous was about 15% or higher.

TABLE 9

| Amount of amorphous (%) | Intrinsic dissolution rate (mg/cm²/min) |
|---|---|
| 0 < Lower than detection limit | 0.0078 |
| 5.6 | 0.0065 |
| 9.8 | 0.0065 |
| 16.8 | 0.0112 |

Example 6

Solubility of the amorphous form and form I crystals of 9-ethyl-6,6-dimethyl-8-(4-morpholin-4-yl-piperidin-1-yl)-11-oxo-6,11-dihydro-5H-benzo[b]carbazole-3-carbonitrile-monohydrochloride was examined using a shake flask method (37° C.). Results are shown in Table 10. It was found that the solubility of the amorphous form was higher than that of the form I crystals.

TABLE 10

| Sample solution | Equilibration time (hour) | Solubility (mg/mL) | |
|---|---|---|---|
| | | Form I crystal | Amorphous |
| First solution for dissolution test (Japanese Pharmacopoeia, 16th edition) | 1 | 0.0012 | 0.0045 |
| | 24 | 0.0013 | 0.0025 |
| Simulated intestinal fluid (SIFsp) | 1 | <Lower than limit of quantitation | <Lower than limit of quantitation |
| | 24 | <Lower than limit of quantitation | <Lower than limit of quantitation |
| Acetate buffer pH 4.5 | 1 | 0.0004 | 0.0005 |
| | 24 | <Lower than limit of quantitation | 0.0004 |
| Phosphate buffer pH 8.0 | 1 | <Lower than limit of quantitation | <Lower than limit of quantitation |
| | 24 | <Lower than limit of quantitation | <Lower than limit of quantitation |
| Solution for dissolution test | 1 | 0.3641 | 1.1506 |
| | 24 | 0.4102 | 1.1552 |
| Water | 1 | 0.0286 | 0.0599 |
| | 24 | 0.0251 | 0.0393 |

Solution for dissolution test: solution obtained by adding 4% of surfactant (Triton-X100) to the first solution for dissolution test
Limit of quantitation: 0.0004 mg/mL

Example 7

(Production of the Starting Material)

Crystals of 9-ethyl-6,6-dimethyl-8-(4-morpholin-4-yl-piperidin-1-yl)-11-oxo-6,11-dihydro-5H-benzo[b]carbazole-3-carbonitrile were obtained using a method similar to the following method (which is described in Example 805 of PTL 2).

500 g of 6-cyano-2-(2-(4-ethyl-3-(4-morpholin-4-yl-piperidin-1-yl)phenyl)propan-2-yl)-1H-indole-3-carboxylic acid was dissolved in a mixture of 9.4 L of DMA, 270 mL of anhydrous acetic acid, and 1170 mL of DIPEA in a nitrogen gas stream and stirred at 90° C. for 1 hour. After being cooled at room temperature, 3.525 L of methanol and then 5.875 L of distilled water were added. Precipitated solids were collected through filtration, washed twice with 1.41 L of a liquid mixture of methanol:water=3:5 and then dried to give the title compound 389.6 g (85%).

(Preparation of Solid Dispersions of the Compound Represented by the Formula (I) by Spray Drying)

Solvents shown in Table 11 were added to vessels containing 2.58 g of the crystals of 9-ethyl-6,6-dimethyl-8-(4-morpholin-4-yl-piperidin-1-yl)-11-oxo-6,11-dihydro-5H-benzo[b]carbazole-3-carbonitrile thus obtained and 5.60 g of the solid polymer shown in Table 8 and the mixtures were stirred until they were dissolved. The liquid mixtures thus obtained were spray dried at about 100° C. and dried under reduced pressure as a post-processing to give amorphous substances of the compound represented by the formula (I) (Example 8) and solid dispersions (Examples 9 to 15).

Conditions during the spray drying are as follows.
Spraying pressure: 25-50 mbar
Inlet temperature: 100° C.

TABLE 11

Solid polymer and solvent used for dissolution

| Example | Solid polymer | Manufacturer | Solvent composition | Solvent volume |
|---|---|---|---|---|
| 8 | None | — | THF | 300 mL |
| 9 | Copovidone | BASF | THF | 300 mL |
| 10 | Solplus | BASF | THF | 300 mL |
| 11 | Hypromellose phthalate | Shin-Etsu Chemical Co., Ltd. | THF | 300 mL |
| 12 | Hypromellose acetate succinate | Shin-Etsu Chemical Co., Ltd. | THF | 300 mL |
| 13 | Methacrylate copolymer L | Evonik Degussa Japan | THF:EtOH (15:1) | 320 mL |
| 14 | Povidone | BASF | THF: EtOH (15:1) | 320 mL |
| 15 | Hypromellose 2910 | Shin-Etsu Chemical Co., Ltd. | THF:$H_2O$ (12:1) | 325 mL |

[Test Example 3] X-Ray Powder Diffraction Analysis

Figure 8:
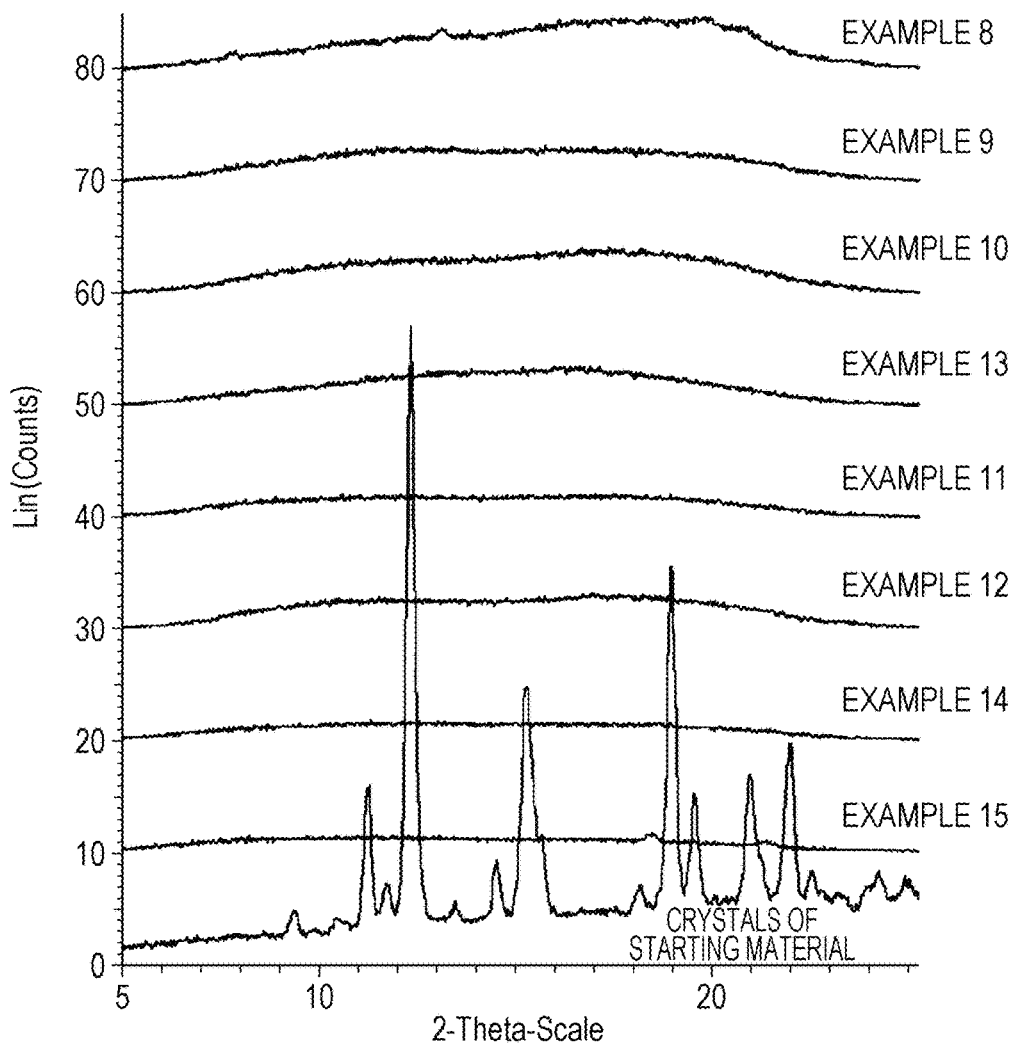
FIG. 8 is a graph showing a result of X-ray powder diffraction measurement on the amorphous form and solid dispersions of the present invention.

On the amorphous substances, the solid dispersions and the crystals as the starting material, of 9-ethyl-6,6-dimethyl-8-(4-morpholin-4-yl-piperidin-1-yl)-11-oxo-6,11-dihydro-5H-benzo[b]carbazole-3-carbonitrile obtained in Examples 8 to 15, X-ray powder diffraction was measured under the following conditions. Results of the measurement are shown in FIG. 8.

Measuring instrument: D8 discover with GADDS (manufactured by Bruker)
Target: Cu
Tube voltage: 40 kV
Tube current: 40 mA
Detection time: 100 sec.
Detection angle: phi 0°, chi 90°
Scanning range: 5 to 25.3°

Halo patterns were observed in all of the X-ray power diffraction patterns of the solid dispersions obtained in Examples 9 to 15, indicating that they are amorphous forms.

[Test Example 4] Accelerated Test

Figure 9:
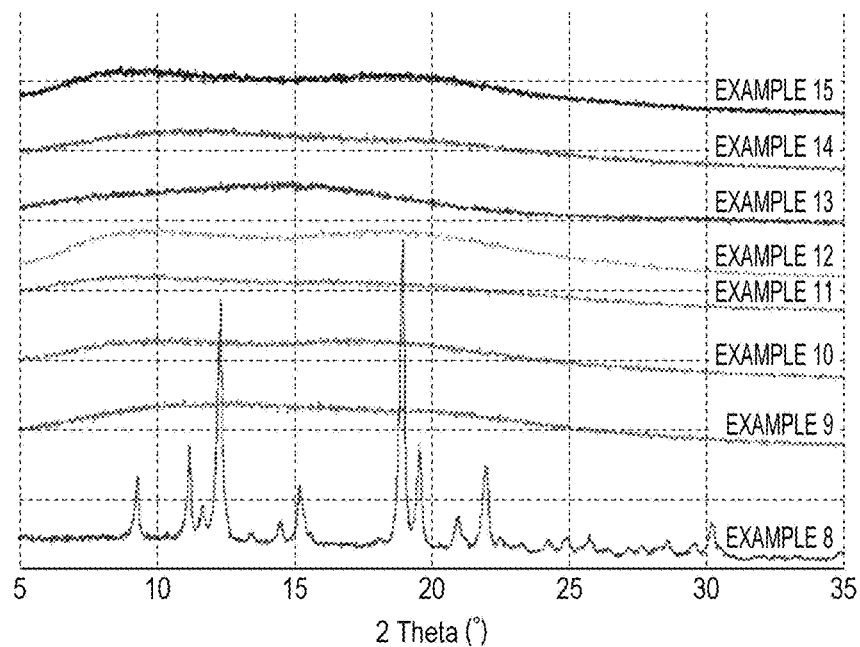
FIG. 9 is a graph showing a result of X-ray powder diffraction measurement on amorphous forms and solid dispersions which have been stored under conditions of 40° C. and 75% RH for 3 months.

Accelerated test was performed on the amorphous substances and the solid dispersions of 9-ethyl-6,6-dimethyl-8-(4-morpholin-4-yl-piperidin-1-yl)-11-oxo-6,11-dihydro-5H-benzo[b]carbazole-3-carbonitrile obtained in Examples 8 to 15 under conditions of 40° C. and 75% RH for 3 months, and X-ray powder diffraction was measured under the following conditions. Results of the measurement are shown in FIG. 9. It was concluded that the solid dispersion hardly crystallized and physically stable.

Measuring instrument: X'Pert-Pro MPD (manufactured by PANalytical)
Target: Cu
Tube voltage: 45 kV
Tube current: 40 mA
Step size: 0.02°
Scan axis: 2θ
Sampling time per step: 43 sec.
Scanning range: 5 to 35°

Test Example 5

The amorphous substances and the solid dispersions of 9-ethyl-6,6-dimethyl-8-(4-morpholin-4-yl-piperidin-1-yl)-11-oxo-6,11-dihydro-5H-benzo[b]carbazole-3-carbonitrile obtained in Examples 8 to 15 were tested under two conditions: i) they were stored in a thermostatic bath set at 40° C. for 3 months, and ii) they were stored in a thermostatic bath set at 40° C. and 75% RH for 3 months in an open state. Residual rates of the principal drugs were measured under following conditions of high performance liquid chromatography. Results of the measurement are shown in Table 13. It was concluded that the amorphous substances and the solid dispersions were chemically stable.

Detector: UV absorptiometer (measurement wavelength: 230 nm)
Column: stainless column of 4.6 mm in inner diameter and 15 cm in length, filled with 3.5 um of octadecylsilyl silica gel for liquid chromatography
Column temperature: fixed temperature about 35° C.
Mobile phase A: mixed solution of acetonitrile/trifluoroacetic acid (2000:1)
Mobile phase B: mixed solution of water/trifluoroacetic acid (2000:1)
Mobile phase supply: controlled concentration gradient with varying mixing ratio of mobile phases A and B as follows.

TABLE 12

| Time after loading (min.) | Mobile phase A (vol %) | Mobile phase B (vol %) |
|---|---|---|
| 0-17 | 5 → 50 | 95 → 50 |
| 17-26 | 50 → 100 | 50 → 0 |
| 26-26.1 | 100 → 5 | 0 → 95 |
| 26.1-30 | 5 | 95 |

Flow rate: 1.0 mL/min.
Loading amount: 10 μL
Sample temperature: fixed temperature about 25° C.

TABLE 13

|  | Retention rate after 3 months at 40° C. | Retention rate after 3 months at 40° C. in 75 % RH |
|---|---|---|
| Example 8 | 99.60 | 99.66 |
| Example 9 | 99.66 | 99.21 |
| Example 10 | 99.79 | 99.71 |
| Example 11 | 99.75 | 99.61 |
| Example 12 | 99.71 | 99.60 |
| Example 13 | 99.63 | 99.59 |
| Example 14 | 99.72 | 99.56 |
| Example 15 | 99.84 | 99.73 |

[Test Example 6] Storage Stability Test

Figure 10:
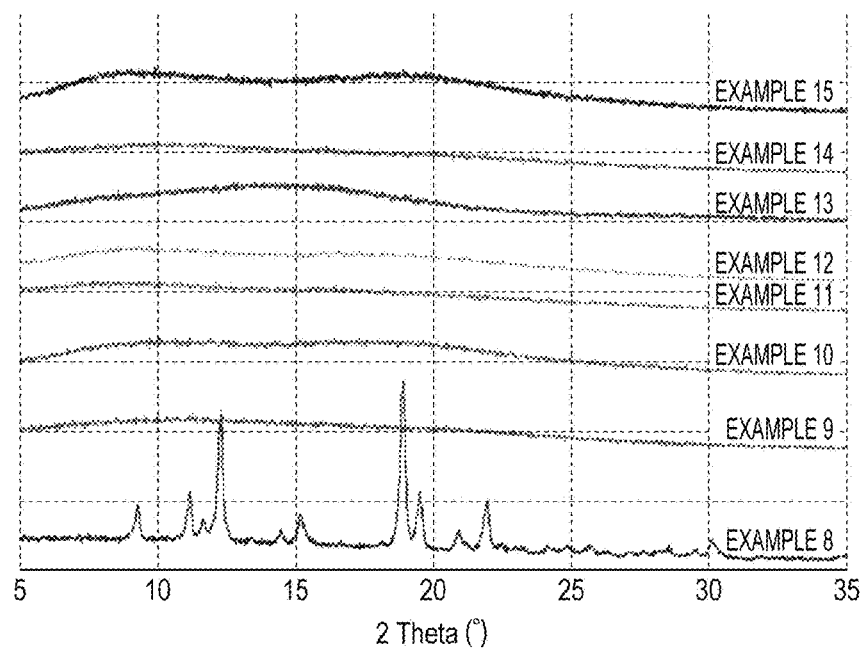
FIG. 10 is a graph showing a result of X-ray powder diffraction measurement on amorphous forms and solid dispersions which have been stored at 25° C. for 1 year.

The amorphous substances and the solid dispersions of 9-ethyl-6,6-dimethyl-8-(4-morpholin-4-yl-piperidin-1-yl)-11-oxo-6,11-dihydro-5H-benzo[b]carbazole-3-carbonitrile obtained in Examples 8 to 15 were subjected to storage stability tests at 25° C. for 1 year. X-ray powder diffraction was measured under the following conditions. Results of the measurement are shown in FIG. 10. It was concluded that the solid dispersions hardly crystallized and were physically stable.

Measuring instrument: X'Pert-Pro MPD (manufactured by PANalytical)
Target: Cu
Tube voltage: 45 kV
Tube current: 40 mA
Step size: 0.02°
Scan axis: 2θ
Sampling time per step: 43 sec.
Scanning range: 5 to 35°

[Test Example 7] Small-Scale Dissolution Test (R. Takano, et al., Pharm. Res. 23:1144-1156 (2006))

Figure 11:
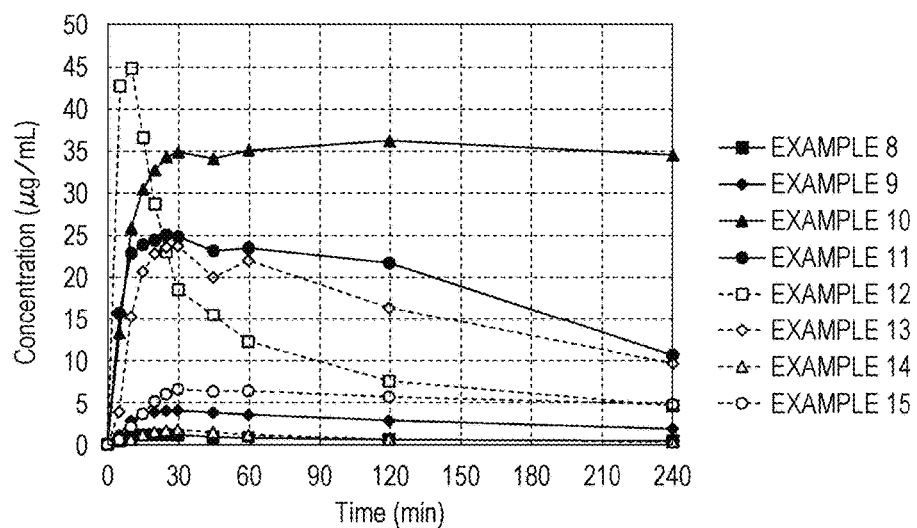
FIG. 11 is a graph showing a result of a dissolution test on the amorphous forms and the solid dispersions of the present invention.

Solubility of the amorphous substances and the solid dispersions of 9-ethyl-6,6-dimethyl-8-(4-morpholin-4-yl-piperidin-1-yl)-11-oxo-6,11-dihydro-5H-benzo[b]carbazole-3-carbonitrile obtained in Examples 8 to 15 in a fasted state simulated intestinal fluid (FaSSIF) was estimated using a small-scale dissolution tester (Vankel Technologies, Inc.) under conditions of 37° C. and a puddle rotation speed of 50 rpm. For each test sample, the concentration of the compound of the formula (I) in the test solution was measured after 5, 10, 15, 20, 25, 30, 45, 60, 120, and 240 minutes under the following conditions of high performance liquid chromatography. Results of the measurement are shown in FIG. 11.

Detector: UV absorptiometer (measurement wavelength: 337 nm)
Column: stainless column of 3.0 mm in inner diameter and 5 cm in length, filled with 3 urn of octadecylsilyl silica gel for liquid chromatography
Column temperature: fixed temperature about 40° C.
Mobile phase A: mixed solution of water/trifluoroacetic acid (1000:1)
Mobile phase B: mixed solution of acetonitrile/trifluoroacetic acid (1000:1)
Mobile phase supply: controlled concentration gradient with varying mixing ratio of mobile phases A and B as follows.

TABLE 14

| Time after loading (min.) | Mobile phase A (vol %) | Mobile phase B (vol %) |
|---|---|---|
| 0-1.5 | 65 | 35 |
| 1.5-1.51 | 65 → 5 | 35 → 95 |
| 1.51-3.0 | 5 | 95 |
| 3.0-3.01 | 5 → 65 | 95 → 35 |
| 3.01-3.5 | 65 | 35 |

Flow rate: 1.0 mL/min.
Loading amount: 10 μL

As a result, it was shown that the solubility of the amorphous substances of 9-ethyl-6,6-dimethyl-8-(4-morpholin-4-yl-piperidin-1-yl)-11-oxo-6,11-dihydro-5H-benzo[b]carbazole-3-carbonitrile is improved by formulating a polymer and that Soluplus (polyvinyl caprolactam-polyvinyl acetate-polyethylene glycol graft copolymer) exhibited the largest effect and the hypromellose acetate succinate, the hypromellose phthalate, and the methacrylate copolymer L exhibited the second largest effect.

Example 16

All ingredients including the form I crystals of 9-ethyl-6,6-dimethyl-8-(4-morpholin-4-yl-piperidin-1-yl)-11-oxo-6,11-dihydro-5H-benzo[b]carbazole-3-carbonitrilemonohydrochloride were weighed at a formulation ratio shown in Table 15. These ingredients except for magnesium stearate and some of sodium starch glycolate were loaded in a high-shear granulator and mixed. Subsequently, wet granulation was performed while adding purified water and the products were subjected to wet sizing and dried under vacuum. The products were then subjected to dry sizing to give granules. The granules thus obtained were mixed with magnesium stearate and the remainder of sodium starch glycolate in a V-shaped mixer to obtain granules for filling

TABLE 15

| Ingredients | Example 16 (wt %) |
|---|---|
| Hydrochloride of the compound of formula (I) | 16.5% |
| Lactose monohydrate | 44.3% |
| Crystalline cellulose | 20.0% |
| Sodium starch glycolate | 6.0% |
| Hydroxypropyl cellulose | 5.0% |
| Sodium lauryl sulfate | 7.7% |
| Magnesium stearate | 0.5% |

Figure 12:
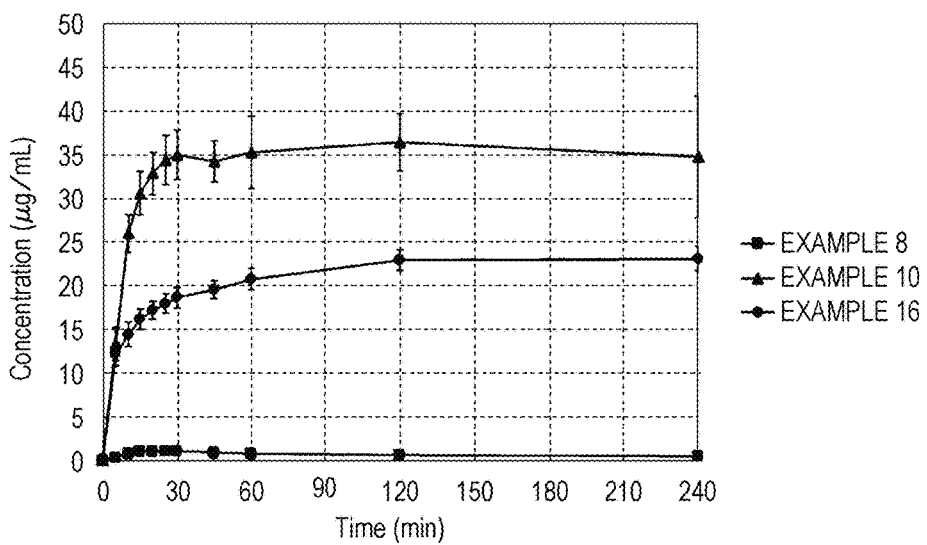
FIG. 12 is a graph comparing elution profiles of the amorphous forms and the solid dispersions of the present invention with an elution profile of a crystalline pharmaceutical preparation of a hydrochloride.

Solubility of Example 16 in FaSSIF was estimated using a small-scale dissolution tester under conditions of 37° C. and a puddle rotation speed of 50 rpm and compared with those of Examples 8 and 10. As a result, as shown in FIG. 12, it was revealed that the solid dispersion using the polyvinyl caprolactam-polyvinyl acetate-polyethylene glycol graft copolymer as a polymer carrier had an improved solubility as compared with the crystalline pharmaceutical preparation of a hydrochloride.

[Test Example 8] Blood Level Measurement

Male beagle dogs purchased from Beijing Marshall Biotechnology Co., Ltd. were used in the test. The animals were not allowed access to food or water 16.5 hours prior to the administration of the drug and injected intravenously with famotidine 2 hours prior to the administration to adjust their stomach pH. The preparations obtained in Examples 10 and 16 were each filled as a test compound in a gelatin capsule in an amount of 5 mg/kg and administered orally. Blood samples were collected over time from 15 minutes to 24 hours after the administration of the pharmaceutical preparations from a cephalic vein in the forearm using a syringe treated with heparin, and were centrifuged to obtain plasma. A blood level of the test compound was then examined (Table 16).

TABLE 16

|  | Maximum blood concentration (ng/mL) | | Area under the curve for blood concentration (ng · hr/mL) | |
| --- | --- | --- | --- | --- |
|  | Average | Standard deviation | Average | Standard deviation |
| Example 10 | 567 | 205 | 2790 | 1030 |
| Example 16 | 264 | 143 | 1140 | 790 |

As compared with the pharmaceutical preparations in the crystalline form, the solid dispersions exhibited high blood levels of the test compounds and it was found that intestinal absorbabilities were improved by about 2.4 times based on the area under the curve for blood level.

As a result of the aforementioned investigation, the amorphous forms of the present invention were stable for a long time at normal temperature and had an improved solubility. In addition, the solid dispersions of the present invention had excellent physical and chemical stabilities and further improved the solubility of the amorphous forms of the present invention. Accordingly, the amorphous forms and the solid dispersions of the present invention are extremely useful for drugs, in particular, dosage forms such as oral drugs which often have problems in bioabsorbabilities.

The invention claimed is:
1. An amorphous form of a compound represented by the formula (I):

[Chemical formula 1]

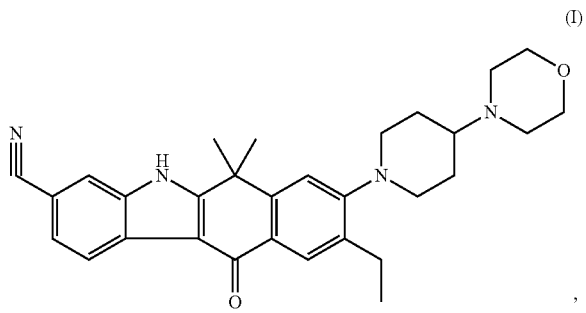

a salt thereof, or a solvate of the compound or a salt thereof.
2. The amorphous form according to claim 1, wherein the amorphous form comprises a salt of the compound.
3. The amorphous form according to claim 1, wherein the salt is a hydrochloride.
4. The amorphous form according to claim 1, wherein the salt is a monohydrochloride.
5. The amorphous form according to claim 1, wherein an exothermic peak is detected between about 190°±5° C. and about 230°±5° C. by a differential scanning calorimetry analysis.
6. The amorphous form according to claim 1, wherein a glass transition temperature is between about 190±5° C. and about 230±5° C.
7. The amorphous form according to claim 1, wherein the amorphous form has an X-ray powder diffraction pattern shown in FIG. 1.
8. A composition comprising amorphous and crystalline forms of a compound represented by the formula (I), a salt thereof, or a solvate of the compound or a salt thereof.
9. A solid dispersion comprising an amorphous form of a compound represented by the formula (I), a salt thereof, or a solvate of the compound or a salt thereof; and an inert carrier.
10. The solid dispersion according to claim 9, wherein the inert carrier is a solid polymer.
11. The solid dispersion according to claim 10, wherein the solid polymer is selected from a polyvinyl caprolactam-polyvinyl acetate-polyethylene glycol graft copolymer, hypromellose phthalate, hypromellose acetate succinate, and a methacrylate copolymer L.
12. The solid dispersion according to claim 10, wherein a weight ratio of the compound represented by the formula (I), the salt thereof, or the solvate of the compound or the salt thereof, as a free form, and the inert carrier is 9:1 to 1:9.
13. A powder, fine granules, granules, a table, or a capsule comprising the solid dispersion according to claim 9.

* * * * *